US010537332B2

(12) United States Patent
Edmiston et al.

(10) Patent No.: US 10,537,332 B2
(45) Date of Patent: Jan. 21, 2020

(54) MEDICAL DEVICE FOR MODIFICATION OF LEFT ATRIAL APPENDAGE AND RELATED SYSTEMS AND METHODS

(71) Applicant: Coherex Medical, Inc., Salt Lake City, UT (US)

(72) Inventors: Daryl R. Edmiston, Draper, UT (US); Clark C. Davis, Holladay, UT (US); John Alexander Martin, Park City, UT (US); Scott D. Miles, Sandy, UT (US)

(73) Assignee: Coherex Medical, Inc., Salt Lake City, UT (US)

( * ) Notice: Subject to any disclaimer, the term of this patent is extended or adjusted under 35 U.S.C. 154(b) by 283 days.

(21) Appl. No.: 15/491,347

(22) Filed: Apr. 19, 2017

(65) Prior Publication Data
US 2017/0215889 A1 Aug. 3, 2017

Related U.S. Application Data

(60) Division of application No. 14/308,695, filed on Jun. 18, 2014, now Pat. No. 9,649,115, which is a (Continued)

(51) Int. Cl.
*A61B 17/12* (2006.01)
*A61F 2/24* (2006.01)
(Continued)

(52) U.S. Cl.
CPC .... *A61B 17/12122* (2013.01); *A61B 17/0057* (2013.01); *A61B 17/12022* (2013.01);
(Continued)

(58) Field of Classification Search
CPC ........ A61B 17/12122; A61B 17/12177; A61B 17/005; A61F 2/013
See application file for complete search history.

(56) References Cited

U.S. PATENT DOCUMENTS 3,095,877 A 7/1963 Rowan
3,874,388 A 4/1975 King et al.
(Continued)

FOREIGN PATENT DOCUMENTS

CA 2627408 5/2008
DE 102006056283 6/2008
(Continued)

OTHER PUBLICATIONS

English Abstract and English machine translation of the Specification and Claims of DE 102006056283. Jun. 5, 2008.
(Continued)

*Primary Examiner* — Richard G Louis
(74) *Attorney, Agent, or Firm* — David L. Stott

(57) ABSTRACT

Devices, methods and systems are provided for occluding an opening within the tissue of a body, such as a left atrial appendage. In one embodiment, a medical device coupled to a delivery catheter includes a fluid flow path that facilitates contrast fluid to pass through the delivery catheter and the medical device to a distal side thereof to provide imaging information as to the position of the medical device positioned in the opening, such as the left atrial appendage. In another embodiment, a medical device is coupled to a delivery catheter, the medical device including flaps adjacent a hub of the medical device that close-off a bore of the hub upon the catheter being detached from the medical device.

20 Claims, 16 Drawing Sheets

Related U.S. Application Data continuation-in-part of application No. 13/666,612, filed on Nov. 1, 2012, now Pat. No. 9,693,781, which is a continuation-in-part of application No. 12/818,046, filed on Jun. 17, 2010, now Pat. No. 8,636,764.

(60) Provisional application No. 61/837,628, filed on Jun. 20, 2013, provisional application No. 61/553,948, filed on Nov. 1, 2011, provisional application No. 61/661,799, filed on Jun. 19, 2012, provisional application No. 61/345,514, filed on May 17, 2010, provisional application No. 61/325,230, filed on Apr. 16, 2010, provisional application No. 61/320,635, filed on Apr. 2, 2010, provisional application No. 61/294,058, filed on Jan. 11, 2010, provisional application No. 61/218,018, filed on Jun. 17, 2009.

(51) Int. Cl.
*A61B 17/00* (2006.01)
*A61F 2/01* (2006.01)

(52) U.S. Cl.
CPC .. *A61B 17/12172* (2013.01); *A61B 17/12177* (2013.01); *A61F 2/013* (2013.01); *A61F 2/2427* (2013.01); *A61B 2017/0069* (2013.01); *A61B 2017/00575* (2013.01); *A61B 2017/00597* (2013.01); *A61B 2017/1205* (2013.01); *A61B 2017/12054* (2013.01); *A61B 2017/12095* (2013.01); *A61F 2002/011* (2013.01); *A61F 2002/016* (2013.01)

(56) References Cited

U.S. PATENT DOCUMENTS

| | | |
|---|---|---|
| 5,171,259 A | 12/1992 | Inoue |
| 5,192,301 A | 3/1993 | Kamiya et al. |
| 5,284,488 A | 2/1994 | Sideris |
| 5,334,217 A | 8/1994 | Das |
| 5,425,733 A | 6/1995 | Schmieding |
| 5,425,740 A | 6/1995 | Hutchinson, Jr. |
| 5,433,727 A | 7/1995 | Sideris |
| 5,792,165 A | 8/1998 | Klieman et al. |
| 5,797,886 A | 8/1998 | Roth et al. |
| 5,861,003 A | 1/1999 | Latson et al. |
| 5,904,703 A | 5/1999 | Gilson |
| 5,910,154 A | 6/1999 | Tsugita et al. |
| 5,935,112 A | 8/1999 | Stevens et al. |
| 5,992,158 A | 11/1999 | Goddard et al. |
| 6,096,027 A | 8/2000 | Layne |
| 6,152,144 A | 11/2000 | Lesh et al. |
| 6,174,322 B1 | 1/2001 | Schneidt |
| 6,231,561 B1 | 5/2001 | Frazier et al. |
| 6,238,403 B1 | 5/2001 | Greene et al. |
| 6,290,674 B1 | 9/2001 | Roue et al. |
| 6,328,727 B1 | 12/2001 | Frazier et al. |
| 6,355,051 B1 | 3/2002 | Sisskind et al. |
| 6,371,971 B1 | 4/2002 | Tsugita et al. |
| 6,398,760 B1 | 6/2002 | Danby |
| 6,419,669 B1 | 7/2002 | Frazier et al. |
| 6,436,088 B2 | 8/2002 | Frazier et al. |
| 6,458,100 B2 | 10/2002 | Roue et al. |
| 6,488,689 B1 | 12/2002 | Kaplan et al. |
| 6,530,934 B1 | 3/2003 | Jacobsen et al. |
| 6,551,303 B1 | 4/2003 | Van Tassel et al. |
| 6,551,341 B2 | 4/2003 | Boylan et al. |
| 6,561,969 B2 | 5/2003 | Frazier et al. |
| 6,585,754 B2 | 7/2003 | Wallace et al. |
| 6,650,923 B1 | 11/2003 | Lesh et al. |
| 6,651,557 B1 | 11/2003 | Frazier et al. |
| 6,652,555 B1 | 11/2003 | Van Tassel et al. |
| 6,652,556 B1 | 11/2003 | Van Tassel et al. |
| 6,666,861 B1 | 12/2003 | Grabek |
| 6,689,150 B1 | 2/2004 | Van Tassel et al. |
| 6,702,825 B2 | 3/2004 | Frazier et al. |
| 6,706,065 B2 | 3/2004 | Langberg et al. |
| 6,712,804 B2 | 3/2004 | Roue et al. |
| 6,730,108 B2 | 5/2004 | Van Tassel et al. |
| 6,746,472 B2 | 6/2004 | Frazier et al. |
| 6,790,229 B1 | 9/2004 | Berreklouw |
| 6,949,113 B2 | 9/2005 | Van Tassel et al. |
| 6,979,344 B2 | 12/2005 | Jones et al. |
| 6,994,092 B2 | 2/2006 | van der Burg et al. |
| 7,011,671 B2 | 3/2006 | Welch |
| 7,014,645 B2 | 3/2006 | Greene, Jr. et al. |
| 7,025,756 B2 | 4/2006 | Frazier et al. |
| 7,044,134 B2 | 5/2006 | Khairkhahan et al. |
| 7,056,294 B2 | 6/2006 | Khairkhahan et al. |
| 7,115,110 B2 | 10/2006 | Frazier et al. |
| 7,128,073 B1 | 10/2006 | van der Burg et al. |
| 7,152,605 B2 | 12/2006 | Khairkhahan et al. |
| 7,169,164 B2 | 1/2007 | Borillo et al. |
| 7,192,439 B2 | 3/2007 | Khairkhahan et al. |
| 7,226,458 B2 | 6/2007 | Kaplan et al. |
| 7,293,562 B2 | 11/2007 | Malecki et al. |
| 7,597,704 B2 | 10/2009 | Frazier et al. |
| 7,608,091 B2 | 10/2009 | Goldfarb et al. |
| 7,717,937 B2 | 5/2010 | Wahr et al. |
| 7,727,189 B2 | 6/2010 | Van Tassel et al. |
| 7,780,645 B2 | 8/2010 | Jones |
| 7,842,054 B2 | 11/2010 | Greene, Jr. et al. |
| 8,142,470 B2 | 3/2012 | Quinn et al. |
| 8,740,934 B2 | 6/2014 | McGuckin, Jr. |
| 2001/0003161 A1 | 6/2001 | Vardi et al. |
| 2001/0037129 A1 | 11/2001 | Thill |
| 2001/0037141 A1 | 11/2001 | Yee et al. |
| 2002/0022860 A1 | 2/2002 | Borillo et al. |
| 2002/0026094 A1 | 2/2002 | Roth |
| 2002/0026217 A1 | 2/2002 | Baker et al. |
| 2002/0035374 A1 | 3/2002 | Borillo et al. |
| 2002/0062130 A1 | 5/2002 | Jugenheimer et al. |
| 2002/0111647 A1 | 8/2002 | Khairkhahan et al. |
| 2002/0177855 A1 | 11/2002 | Greene, Jr. et al. |
| 2002/0183787 A1 | 12/2002 | Wahr et al. |
| 2003/0014075 A1 | 1/2003 | Rosenbluth et al. |
| 2003/0023266 A1 | 1/2003 | Borillo et al. |
| 2003/0055455 A1 | 3/2003 | Yang et al. |
| 2003/0057156 A1 | 3/2003 | Peterson et al. |
| 2003/0120337 A1 | 6/2003 | Van Tassel et al. |
| 2003/0125790 A1 | 7/2003 | Fastovsky et al. |
| 2003/0153935 A1 | 8/2003 | Mialhe |
| 2003/0171739 A1 | 9/2003 | Murphy et al. |
| 2003/0181942 A1 | 9/2003 | Sutton et al. |
| 2003/0187474 A1 | 10/2003 | Keegan et al. |
| 2003/0191526 A1 | 10/2003 | Van Tassel et al. |
| 2003/0195555 A1 | 10/2003 | Khairkhahan et al. |
| 2003/0199923 A1 | 10/2003 | Khairkhahan et al. |
| 2003/0204203 A1 | 10/2003 | Khairkhahan et al. |
| 2003/0208227 A1 | 11/2003 | Thomas |
| 2003/0212432 A1 | 11/2003 | Khairkhahan et al. |
| 2003/0220667 A1 | 11/2003 | Van Der Burg et al. |
| 2004/0034366 A1 | 2/2004 | Van Der Burg et al. |
| 2004/0049224 A1 | 3/2004 | Buehlmann et al. |
| 2004/0098028 A1 | 5/2004 | Martinez |
| 2004/0098031 A1 | 5/2004 | van der Burg et al. |
| 2004/0122467 A1 | 6/2004 | Van Tassel et al. |
| 2004/0127935 A1 | 7/2004 | Van Tassel et al. |
| 2004/0153120 A1 | 8/2004 | Seifert et al. |
| 2004/0181237 A1 | 9/2004 | Forde et al. |
| 2004/0215230 A1 | 10/2004 | Frazier et al. |
| 2004/0254594 A1 | 12/2004 | Alfaro |
| 2004/0260317 A1 | 12/2004 | Bloom |
| 2004/0267191 A1 | 12/2004 | Gifford, III et al. |
| 2005/0004652 A1 | 1/2005 | Van Der Burg et al. |
| 2005/0033409 A1 | 2/2005 | Burke et al. |
| 2005/0038470 A1 | 2/2005 | Van Der Burg et al. |
| 2005/0043759 A1 | 2/2005 | Chanduszko |
| 2005/0049573 A1 | 3/2005 | Van Tassel et al. |
| 2005/0049681 A1 | 3/2005 | Greenhalgh et al. |
| 2005/0060017 A1 | 3/2005 | Fishell et al. |
| 2005/0065589 A1 | 3/2005 | Schneider et al. |
| 2005/0075665 A1 | 4/2005 | Brenzel et al. |
| 2005/0085843 A1 | 4/2005 | Opolski et al. |

(56) References Cited

U.S. PATENT DOCUMENTS

| | | |
|---|---|---|
| 2005/0090860 A1 | 4/2005 | Paprocki |
| 2005/0113861 A1 | 5/2005 | Corcoran et al. |
| 2005/0149173 A1 | 7/2005 | Hunter et al. |
| 2005/0177182 A1 | 8/2005 | van der Burg et al. |
| 2005/0192616 A1 | 9/2005 | Callister et al. |
| 2005/0192627 A1 | 9/2005 | Whisenant et al. |
| 2005/0222533 A1 | 10/2005 | Chanduszko et al. |
| 2005/0234540 A1 | 10/2005 | Peavey et al. |
| 2005/0234543 A1 | 10/2005 | Glaser et al. |
| 2005/0251144 A1 | 11/2005 | Wilson et al. |
| 2005/0256532 A1 | 11/2005 | Nayak et al. |
| 2005/0267524 A1 | 12/2005 | Chanduszko |
| 2005/0288706 A1 | 12/2005 | Widomski et al. |
| 2006/0000443 A1 | 1/2006 | Kado et al. |
| 2006/0004433 A1 | 1/2006 | Greenberg et al. |
| 2006/0009798 A1 | 1/2006 | Callister |
| 2006/0009800 A1 | 1/2006 | Christianson et al. |
| 2006/0020327 A1 | 1/2006 | Lashinski et al. |
| 2006/0036282 A1 | 2/2006 | Wahr et al. |
| 2006/0052816 A1 | 3/2006 | Bates et al. |
| 2006/0122646 A1 | 6/2006 | Corcoran et al. |
| 2006/0149299 A1 | 7/2006 | Greene et al. |
| 2006/0149307 A1 | 7/2006 | Durgin |
| 2006/0149314 A1 | 7/2006 | Borillo et al. |
| 2006/0155323 A1 | 7/2006 | Porter et al. |
| 2006/0206148 A1 | 9/2006 | Khairkhahan et al. |
| 2006/0210816 A1 | 9/2006 | Finley |
| 2006/0217761 A1 | 9/2006 | Opolski |
| 2006/0229668 A1 | 10/2006 | Prestezog et al. |
| 2006/0276839 A1 | 12/2006 | McGuckin, Jr. |
| 2007/0027456 A1 | 2/2007 | Gartner et al. |
| 2007/0066993 A1 | 3/2007 | Kreidler |
| 2007/0073247 A1 | 3/2007 | Ewaschuk |
| 2007/0083230 A1 | 4/2007 | Javois |
| 2007/0083232 A1 | 4/2007 | Lee |
| 2007/0088388 A1 | 4/2007 | Opolski et al. |
| 2007/0112382 A1 | 5/2007 | Thill et al. |
| 2007/0123934 A1 | 5/2007 | Whisenant et al. |
| 2007/0129753 A1 | 6/2007 | Quinn et al. |
| 2007/0129757 A1 | 6/2007 | Armstrong |
| 2007/0135826 A1 | 6/2007 | Zaver et al. |
| 2007/0149995 A1 | 6/2007 | Quinn et al. |
| 2007/0167981 A1 | 7/2007 | Opolski et al. |
| 2007/0173885 A1 | 7/2007 | Cartier et al. |
| 2007/0179527 A1 | 8/2007 | Eskuri et al. |
| 2007/0179583 A1 | 8/2007 | Goetzinger et al. |
| 2007/0191884 A1 | 8/2007 | Eskridge et al. |
| 2007/0198059 A1 | 8/2007 | Patel et al. |
| 2007/0213766 A1 | 9/2007 | Ravikumar |
| 2007/0237720 A1 | 10/2007 | Padilla et al. |
| 2007/0270891 A1 | 11/2007 | McGuckin |
| 2007/0276415 A1 | 11/2007 | Kladakis et al. |
| 2008/0039929 A1 | 2/2008 | Davis et al. |
| 2008/0119891 A1 | 5/2008 | Miles et al. |
| 2008/0215086 A1 | 9/2008 | Olsen et al. |
| 2008/0249562 A1* | 10/2008 | Cahill ................ A61B 17/0057 606/215 |
| 2009/0025820 A1 | 1/2009 | Adams |
| 2009/0069840 A1 | 3/2009 | Hallisey |
| 2009/0099596 A1 | 4/2009 | McGuckin, Jr. et al. |
| 2009/0105747 A1 | 4/2009 | Chanduszko et al. |
| 2009/0112050 A1 | 4/2009 | Farnan et al. |
| 2009/0112249 A1 | 4/2009 | Miles et al. |
| 2009/0171386 A1 | 7/2009 | Amplatz et al. |
| 2009/0177163 A1 | 7/2009 | King et al. |
| 2009/0192518 A1 | 7/2009 | Golden et al. |
| 2009/0228038 A1 | 9/2009 | Amin |
| 2009/0299338 A1 | 12/2009 | di Palma |
| 2009/0318948 A1 | 12/2009 | Linder et al. |
| 2010/0191279 A1 | 7/2010 | Kassab et al. |
| 2010/0228279 A1* | 9/2010 | Miles ................ A61B 17/0057 606/198 |
| 2010/0228285 A1 | 9/2010 | Miles et al. |
| 2010/0234878 A1 | 9/2010 | Hruska et al. |
| 2010/0324585 A1 | 12/2010 | Miles et al. |
| 2010/0324586 A1 | 12/2010 | Mlles et al. |
| 2010/0324587 A1 | 12/2010 | Miles et al. |
| 2010/0324588 A1 | 12/2010 | Miles et al. |
| 2011/0022079 A1 | 1/2011 | Miles et al. |
| 2011/0046658 A1 | 2/2011 | Connor et al. |
| 2011/0054515 A1 | 3/2011 | Bridgeman et al. |
| 2011/0208233 A1 | 8/2011 | McGuckin, Jr. et al. |
| 2012/0316584 A1 | 12/2012 | Miles et al. |

FOREIGN PATENT DOCUMENTS

| | | |
|---|---|---|
| EP | 1266630 | 12/2002 |
| EP | 1358850 | 11/2003 |
| EP | 1523957 | 4/2005 |
| EP | 1741393 | 1/2007 |
| EP | 1768604 | 4/2007 |
| EP | 1659988 | 2/2010 |
| JP | 2008536620 | 9/2008 |
| JP | 2010500917 | 1/2010 |
| WO | 1999/33402 | 7/1999 |
| WO | 00/27292 | 5/2000 |
| WO | 2001/93920 | 12/2001 |
| WO | 2002/071977 | 9/2002 |
| WO | 2003/028802 | 4/2003 |
| WO | 2004045393 | 6/2004 |
| WO | 2004/100803 | 11/2004 |
| WO | 2005053547 | 6/2005 |
| WO | 2005099365 | 10/2005 |
| WO | 2006/033641 | 3/2006 |
| WO | 2006047748 | 5/2006 |
| WO | 2007/054116 | 5/2007 |
| WO | 2007/147145 | 12/2007 |
| WO | WO 2008150346 | 12/2008 |
| WO | 2010/081033 | 7/2010 |
| WO | 2010/148246 | 12/2010 |

OTHER PUBLICATIONS

Office Action and English Translation issued in JP2012-516313 dated Mar. 25, 2014.
International Search Report dated Feb. 7, 2013 for International Application No. PCT/US2012/063074 (5 pages).
International Search Report dated Apr. 26, 2010 for International Application No. PCT/US2010/020549 (7 pages).
International Search Report dated May 7, 2010 for International Application No. PCT/US2010/020547 (4 pages).
International Search Report dated May 6, 2010 for International Application No. PCT/US2010/020539 (5 pages).
International Search Report dated Jun. 15, 2009 for International Application No. PCT/US2008/080374 (7 pages).
Supplemental European Search Report dated Jan. 3, 2019 for EP App. No. 18185291.4 (6 pages).
European Search Report dated Aug. 6, 2018 for EP App. No. 18157669.5 (15 pages).

* cited by examiner

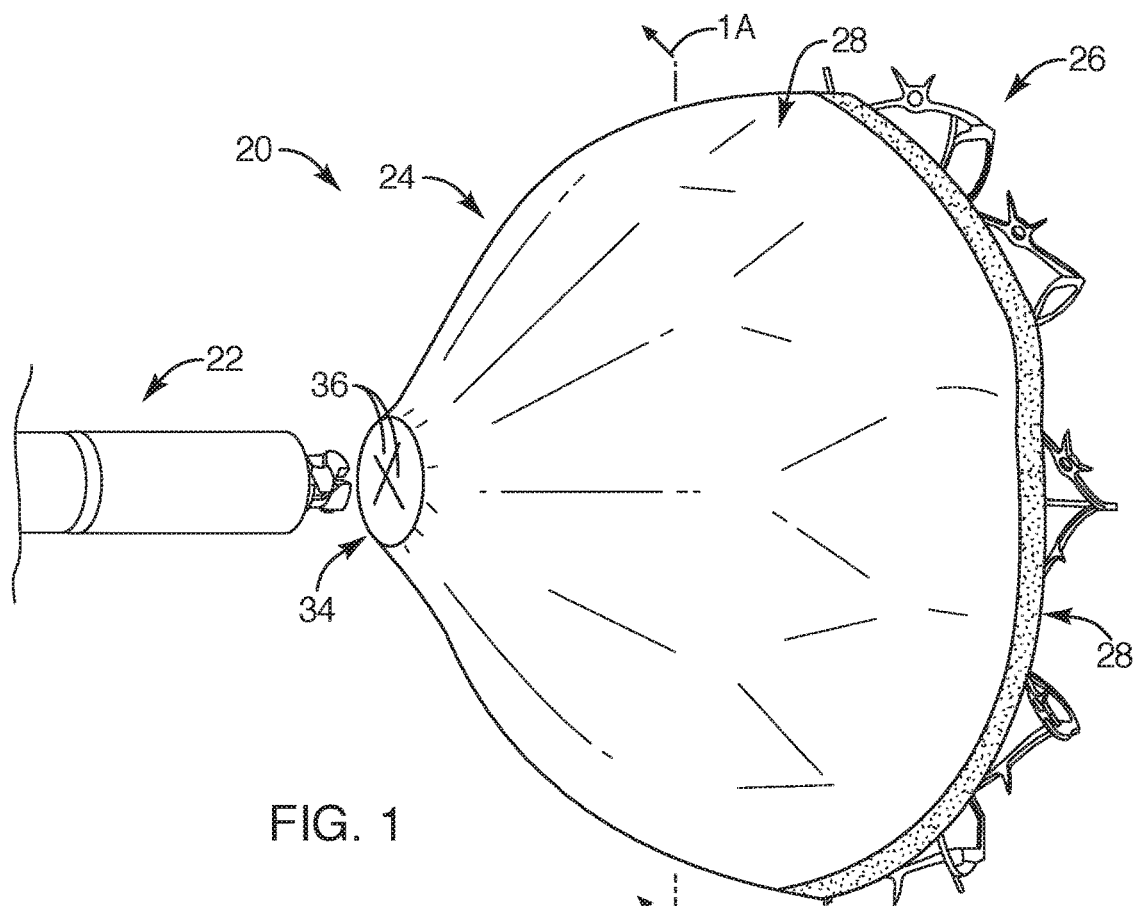
FIG. 1
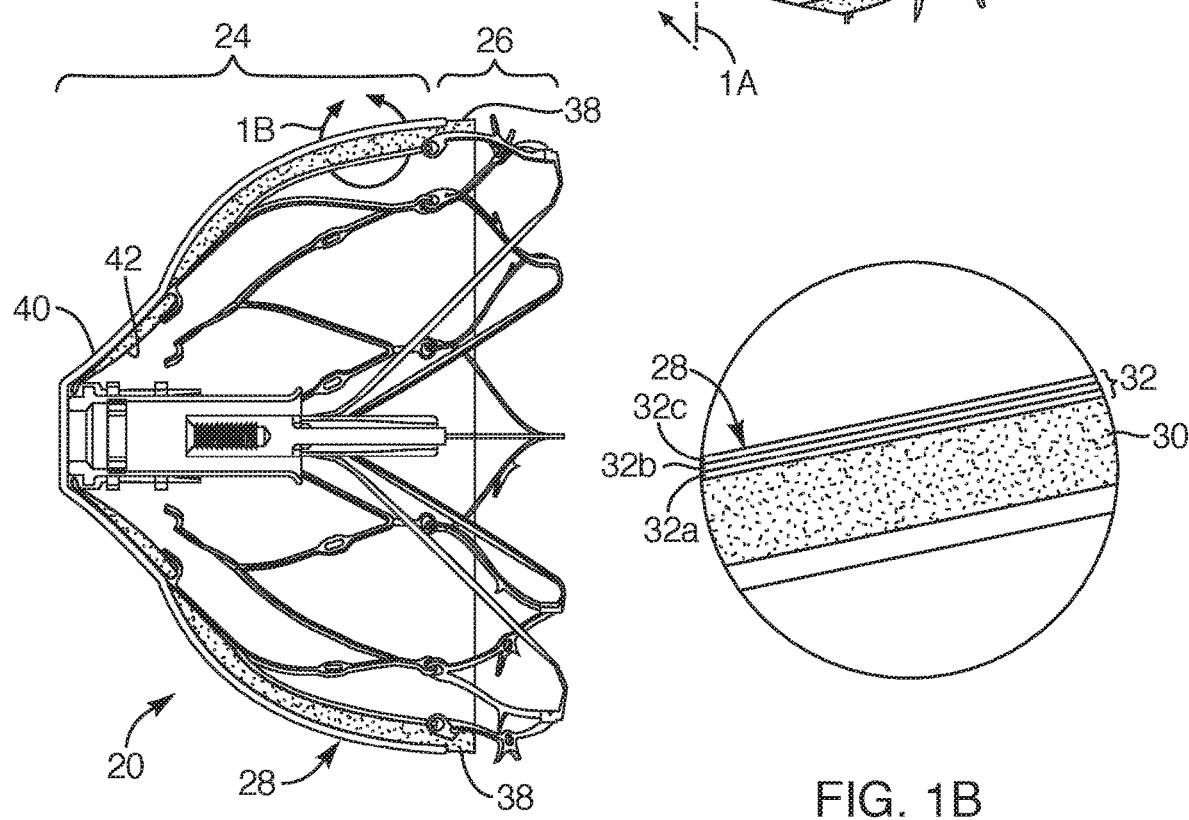
FIG. 1A
FIG. 1B

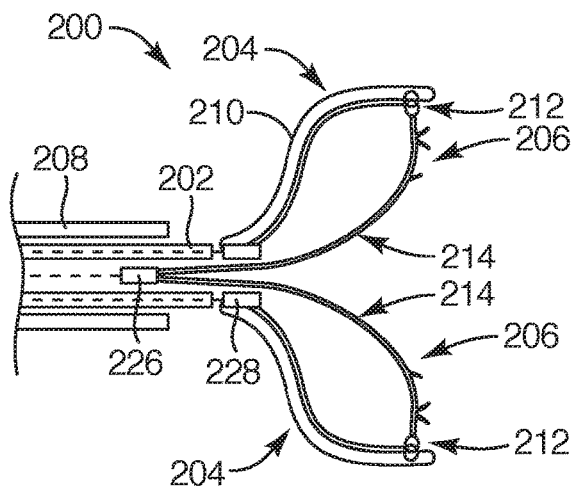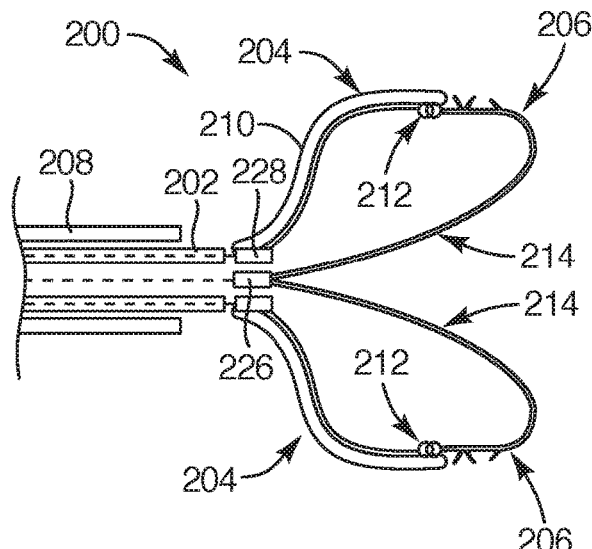
FIG. 14A  FIG. 14B
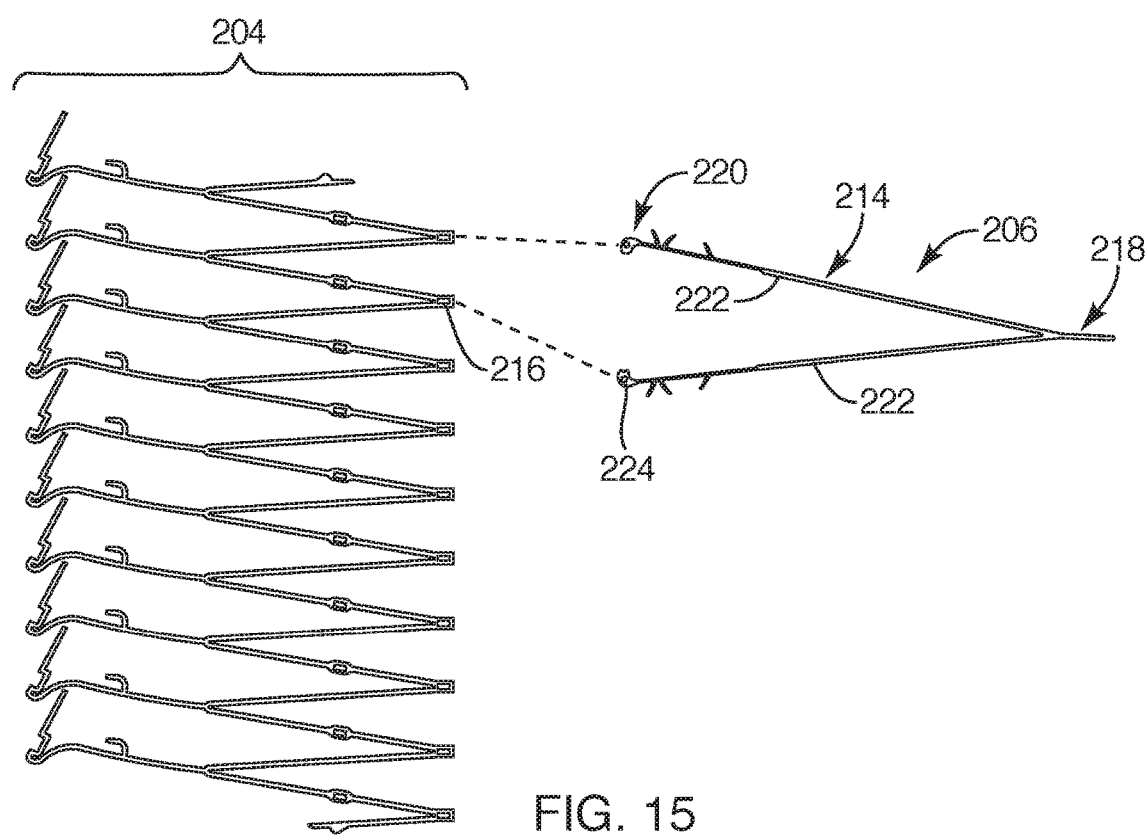
FIG. 15

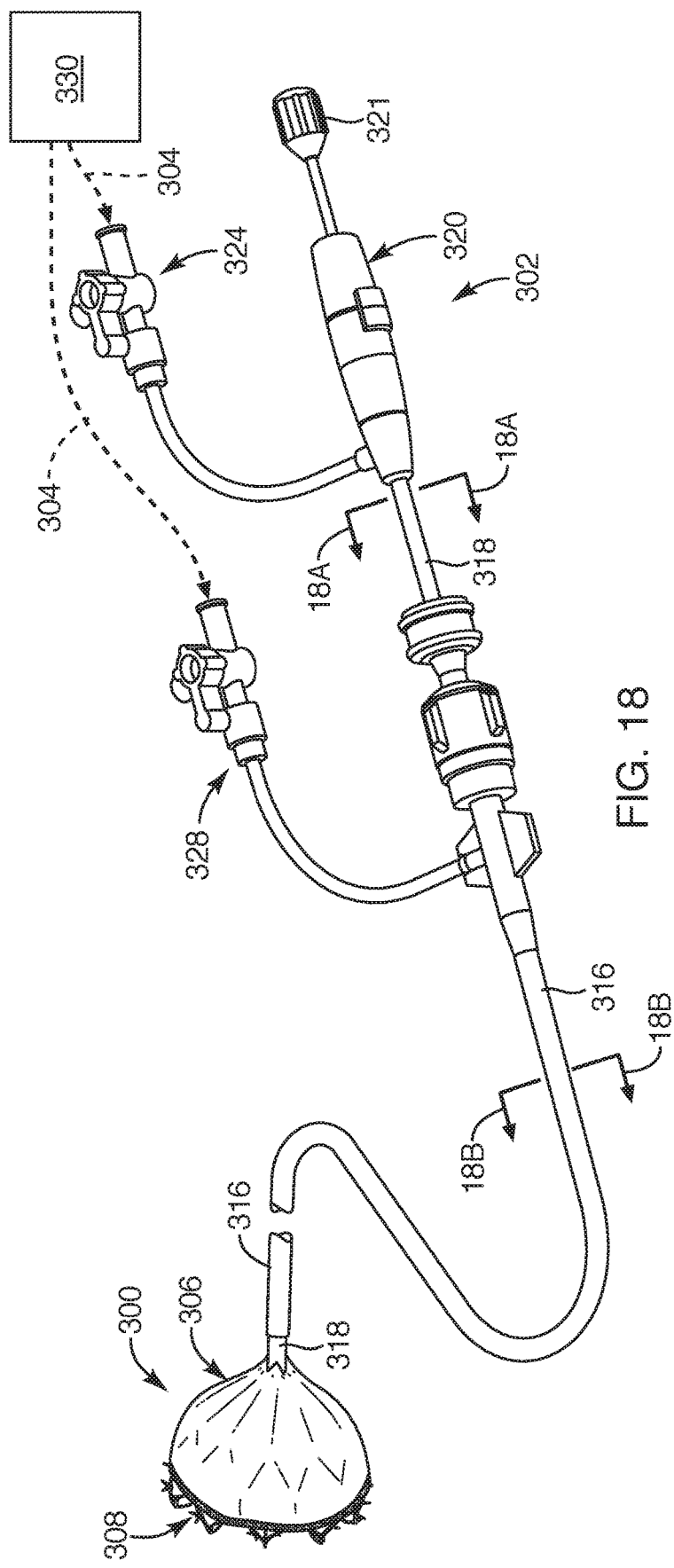
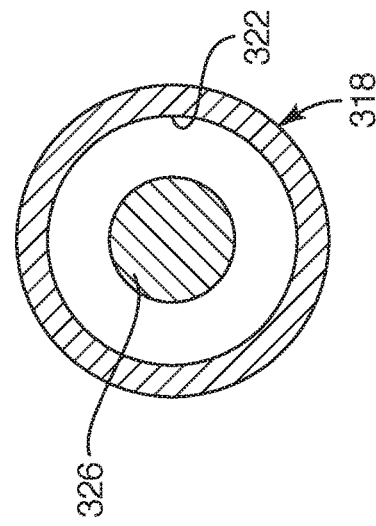
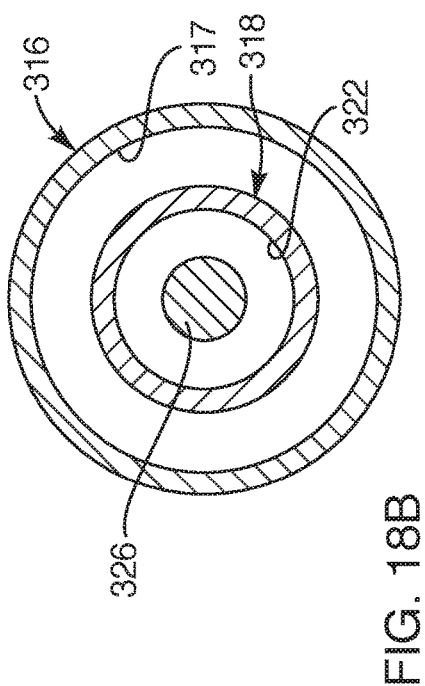
FIG. 18
FIG. 18A
FIG. 18B

MEDICAL DEVICE FOR MODIFICATION OF LEFT ATRIAL APPENDAGE AND RELATED SYSTEMS AND METHODS

CROSS-REFERENCE TO RELATED APPLICATIONS

The present application is a divisional of U.S. patent application Ser. No. 14/308,695, filed on Jun. 18, 2014, which claims the benefit of U.S. Provisional Application No. 61/837,628, filed on Jun. 20, 2013. Further, U.S. patent application Ser. No. 14/308,695 also claims benefit to, and is a continuation-in-part of, U.S. patent application Ser. No. 13/666,612, filed Nov. 1, 2012, which in turn claims benefit to U.S. Provisional Application No. 61/553,948, filed on Nov. 1, 2011, and U.S. Provisional Application No. 61/661,799, filed on Jun. 19, 2012. Further, the above-listed U.S. patent application Ser. No. 13/666,612 claims benefit to, and is a continuation-in-part of, U.S. patent application Ser. No. 12/818,046, filed on Jun. 17, 2010, now issued as U.S. Pat. No. 8,636,764, which in turn claims benefit to the following U.S. Provisional Patent Applications: U.S. Provisional Application No. 61/345,514, filed on May 17, 2010; U.S. Provisional Application No. 61/325,230, filed on Apr. 16, 2010; U.S. Provisional Application No. 61/320,635, filed on Apr. 2, 2010; U.S. Provisional Application No. 61/294,058, filed on Jan. 11, 2010; and U.S. Provisional Application No. 61/218,018, filed on Jun. 17, 2009. The disclosures of each application listed above are incorporated by reference herein in their entireties.

TECHNICAL FIELD

The present invention relates generally to the occlusion or modification of tissue openings or appendages and, more specifically, to devices, systems and methods for occluding or otherwise structurally altering such openings and appendages including, for example, left atrial appendages.

BACKGROUND

The upper chambers of the heart, the atria, have appendages attached to each of them. For example, the left atrial appendage is a feature of all human hearts. The physiologic function of such appendages is not completely understood, but they do act as a filling reservoir during the normal pumping of the heart. The appendages typically protrude from the atria and cover an external portion of the atria. Atrial appendages differ substantially from one to another. For example, one atrial appendage may be configured as a tapered protrusion while another atrial appendage may be configured as a re-entrant, sock-like hole. The inner surface of an appendage is conventionally trabeculated with cords of muscular cardiac tissue traversing its surface with one or multiple lobes.

The atrial appendages appear to be inert while blood is being pumped through them during normal heart function. In other words, the appendages don't appear to have a noticeable effect on blood pumped through them during normal heart function. However, in cases of atrial fibrillation, when the atria go into arrhythmia, blood may pool and thrombose inside of the appendages. Among other things, this can pose a stroke risk when it occurs in the left appendage since the thrombus may be pumped out of the heart and into the cranial circulation once normal sinus rhythm is restored following arrhythmia events.

Historically, appendages have sometimes been modified surgically to reduce the risk imposed by atrial fibrillation. In recent years devices which may be delivered percutaneously into the left atrial appendage have been introduced. The basic function of these devices is to exclude the volume within the appendage with an implant which then allows blood within the appendage to safely thrombose and then to be gradually incorporated into cardiac tissue. This process, coupled with the growth of endothelium over the face of the device, can leave a smooth, endothelialized surface where the appendage is located. In comparison to surgical procedures, devices implanted percutaneously are a less invasive means for addressing the problems associated with the left atrial appendage.

However, due to the wide variability of the ostium size and volume of the left atrial appendage, current implantable devices conventionally include a structure that cannot meet such variability, resulting in inadequate devices for many left atrial appendage anatomies. Further, such implantable devices are substantially limited by the orientation by which they can successfully be deployed. As such, it would be advantageous to provide a percutaneous system, method and/or device that addresses, for example, the issues of implant orientation, the variability in sizes and shapes of the left atrial appendage, or all of these, in order to provide high success in left atrial appendage modification. It would also be desirable to provided a device, system and method that enable easy positioning and repositioning of the device relative to the structure being modified or occluded including the positioning (or repositioning) of an occluder portion independent of other components or features of the device.

A variety of features and advantages will be apparent to those of ordinary skill in the art upon reading the description of various embodiments set forth below.

BRIEF SUMMARY OF THE INVENTION

Embodiments of the present invention are directed to various devices, systems and methods of occluding an opening in the tissue of a body. For example, in one embodiment, a medical device system for modifying a left atrial appendage ("LAA") of a heart is provided. The medical device system includes a sheath and a delivery system. The sheath includes a length and defines a sheath lumen extending through the length of the sheath. The delivery system includes a delivery catheter that extends between a proximal end and a distal end, a handle coupled to the proximal end of the delivery catheter, and a medical device operatively coupled to the handle and coupled to the distal end of the delivery catheter. The medical device includes a hub having a bore that defines an axis, an occluder portion, and an anchor portion. The occluder portion is coupled to the hub and is configured to be moved to an occluder non-deployed position with the occluder portion within a distal portion of the sheath, and the occluder portion configured to be moved to an occluder deployed position upon the sheath being moved proximally relative to the occluder portion. The anchor portion extends between a first end and a second end. The first end is configured to be operatively coupled to the handle and the second end is configured to be coupled to the occluder portion. With this arrangement, upon the occluder portion being in the occluder deployed position, the anchor portion is configured to move relative to the occluder portion between an anchor non-deployed position and an anchor deployed position.

In one embodiment, the second end of the anchor portion is coupled to the occluder portion with a hinge arrangement such that the anchor portion pivots relative to the occluder portion upon the anchor portion being moved between the anchor non-deployed position and the anchor deployed position. In another embodiment, the second end of the anchor portion is pivotably coupled to the occluder portion. In still another embodiment, the first end of the anchor portion is moveable along the axis of the hub to move the anchor portion between the anchor non-deployed position and the anchor deployed position. In another embodiment, the handle includes a plunger shaft that is moveable between a first position and a second position that corresponds with the anchor non-deployed position and the anchor deployed position, respectively.

In another embodiment, the anchor portion includes multiple anchor actuator arms that each extend to a v-extension such that the v-extension includes hooks to engage tissue of the LAA. In another embodiment, the anchor portion includes an anchor zig-zag portion hingably coupled to the occluder portion. In still another embodiment, the occluder portion includes an occluder zig-zag portion and the anchor portion includes an anchor zig-zag portion. In yet another embodiment, the occluder portion includes a tissue growth member extending over a proximal face of the occluder portion and extending over a portion of the anchor portion.

In another embodiment, the distal end of the delivery catheter is threadably connected to the medical device. In another embodiment, the delivery catheter includes an actuator shaft and multiple fingers. The actuator shaft is configured to be actuated by actuation of the handle. Further, the multiple fingers extend distally from the distal end of the delivery catheter such that the multiple fingers extend over the actuator shaft so that the multiple fingers maintain a latched position to the hub. Furthermore, in another embodiment, the medical device is configured to detach from the delivery catheter upon proximal movement of the actuator shaft to a position proximal of the multiple fingers such that the multiple fingers collapse to an inward unlatched position. In yet another embodiment, the sheath includes an imaging device at a distal end of the sheath.

In accordance with another embodiment of the present invention, a medical device for modifying an LAA of a heart. The medical device includes a hub defining an axis, an occluder portion, and an anchor portion. The occluder portion is coupled to the hub. Further, the occluder portion is independently moveable relative to the anchor portion between an occluder non-deployed position and an occluder deployed position. The anchor portion is hingably coupled to the occluder portion such that the anchor portion is pivotable relative to the occluder portion between an anchor non-deployed position and an anchor deployed position upon the occluder portion being in the occluder deployed position.

In one embodiment, the anchor portion includes anchor actuator arms with a portion actuatable substantially along the axis of the hub to move the anchor portion between the anchor non-deployed position and the anchor deployed position. In another embodiment, the anchor portion includes multiple anchor actuator arms each extending to a v-extension such that the v-extension includes hooks to engage tissue of the LAA. In still another embodiment, the anchor portion includes an anchor zig-zag portion hingably coupled to the occluder portion. In another embodiment, the occluder portion includes an occluder zig-zag portion and the anchor portion includes an anchor zig-zag portion, and the occluder zig-zag portion is hingably coupled to the anchor zig-zag portion.

In another embodiment, the occluder portion includes a tissue growth member that extends over a proximal face of the occluder portion and extends over a portion of the anchor portion. In still another embodiment, the medical device further includes a sheath configured to move the occluder portion between the occluder non-deployed configuration and the occluder deployed configuration, the sheath including an imaging device at a distal end of the sheath.

In accordance with another embodiment of the present invention, a method for modifying an LAA of a heart is provided. The method includes: advancing a medical device coupled to a distal end of a delivery catheter through a sheath positioned in the vasculature and into the LAA of the heart, the medical device including an occluder portion and an anchor portion, the anchor portion coupled to the occluder portion; deploying the occluder portion of the medical device from the sheath in the LAA with the anchor portion maintaining a non-deployed position; and actuating the anchor portion of the medical device between the non-deployed position and a deployed position while the occluder portion of the medical device is deployed.

In another embodiment, the method step of actuating the anchor portion includes pivoting the anchor portion at a hinged coupling between the anchor portion and the occluder portion. In another embodiment, the method step of actuating the anchor portion includes actuating actuator arms of the anchor portion substantially along an axis of the medical device. In still another embodiment, the method step of deploying the occluder portion includes manually withdrawing the sheath from over the occluder portion of the medical device. In another embodiment, the method further includes disengaging the medical device from fingers extending from the distal end of the delivery catheter by proximally moving an actuator shaft from the medical device to collapse the fingers from a hub of the medical device. In still another embodiment, the method further includes imaging the medical device relative to the LAA from a distal end of the sheath.

In accordance with another embodiment of the present invention, a medical device for modifying an LAA of a heart includes an occluder frame and an anchor portion. The occluder frame includes a proximal end and a distal end with the proximal end coupled to a hub. The anchor portion includes a first end and a second end. The second end is hingably coupled to the distal end of the occluder frame and the first end is coupled to a collar arrangement. The collar arrangement is moveable co-axially relative to an axis of the hub to move the anchor portion between an anchor deployed configuration and an anchor non-deployed configuration.

In one embodiment, the anchor portion includes a zig-zag anchor portion. In another embodiment, the zig-zag anchor portion includes tines extending therefrom, the tines configured to engage tissue within the LAA. In another embodiment, the anchor portion includes loop extensions.

In another embodiment, the occluder frame includes a zig-zag occluder portion. In one embodiment, the zig-zag occluder portion includes face struts extending proximally therefrom toward the hub. In another embodiment, the medical device includes a tissue growth member attached to the occluder frame. In one embodiment, the tissue growth member extends distal the distal end of the occluder frame.

In another embodiment, the anchor portion is hingably coupled to the occluder portion to facilitate pivoting the anchor portion relative to the occluder portion between the anchor deployed configuration and the anchor non-deployed configuration. In another embodiment, the anchor portion includes a first hinge arrangement and a second hinge arrangement. In one embodiment, the anchor portion includes a flexure portion distal the zig-zag anchor portion.

In another embodiment, the collar arrangement is a splined sleeve. In another embodiment, the medical device further includes a spring coupled to a proximal end of the hub and is configured to close-off an opening defined in the hub. Such a spring may include a clover configuration. In another embodiment, the medical device further includes a delivery catheter configured to removably couple to the hub. The delivery catheter includes a threaded connector and a collet. The threaded connector is configured to be threaded to the collar arrangement. The collet includes collet fingers extending distally from the collet. The collet fingers are engageable with the hub. The threaded connector, upon being unthreaded from the collar arrangement, is moveable proximally through the collet such that the collet fingers collapse to disengage from the hub.

In accordance with another embodiment of the present invention, a method for modifying a left atrial appendage ("LAA") of a heart is provided. The method includes: positioning a medical device coupled to a distal end of a delivery catheter within the LAA of the heart such that the medical device includes an occluder portion having a substantially non-permeable material that substantially blocks fluid from exiting the LAA; injecting contrast fluid through the delivery catheter and through a hub of the medical device and into the LAA; viewing the contrast fluid injected into the LAA with an imaging device; and determining whether the medical device is properly positioned in the LAA upon viewing that the contrast fluid in the LAA with the non-permeable material of the medical device is substantially maintaining the contrast fluid in the LAA.

In another embodiment, the method further includes the step of advancing the medical device through a sheath in the vasculature and to the LAA of the heart. In another embodiment, the step of injecting includes injecting the contrast fluid through a fluid port in a handle coupled to a proximal end of the delivery catheter such that the contrast fluid flows through a lumen defined within and along a longitudinal length of the delivery catheter. In still another embodiment, the method step of positioning includes engaging an anchor portion of the medical device to tissue in the LAA. In another embodiment, the method step of injecting contrast fluid includes injecting contrast fluid with an injection member. In yet another embodiment, the method step of viewing includes viewing the contrast fluid with an imaging device.

In another embodiment, the method step of injecting includes injecting the fluid along a flow path that is defined at least through the hub of the medical device such that the contrast fluid exits a distal side of the hub of the medical device and into the LAA. In another embodiment, the method step of determining includes determining whether there are gaps between an outer periphery of the medical device and the tissue of the LAA by viewing the contrast fluid. In another embodiment, the method further includes the step of re-positioning the medical device in the LAA upon determining contrast fluid is not being substantially maintained within the LAA with the medical device.

In another embodiment, the method step of positioning the medical device includes deploying the occluder portion of the medical device and, then, upon the occluder portion being in an expanded, deployed position, actuating an anchor portion of the medical device from a retracted position to an anchor deployed position. In still another embodiment, the method step of positioning includes actuating an anchor portion of the medical device between a retracted position and an anchor deployed position such that a portion of the anchor portion is moveable through the hub of the medical device. In yet another embodiment, the method step of actuating the anchor portion includes pivoting the anchor portion at a hinged coupling between the anchor portion and the occluder portion. In still another embodiment, the method step of actuating the anchor portion includes actuating actuator arms of the anchor portion substantially along an axis of the medical device. In another embodiment, the method step of positioning the medical device includes substantially occluding the LAA, wherein the non-permeable material of the occluder portion includes ePTFE.

In accordance with another embodiment of the present invention, a medical device system for modifying a left atrial appendage ("LAA") of a heart that facilitates imaging of the LAA with contrast fluid and an imaging device is provided. The medical device system includes a handle, a delivery catheter, and a medical device. The handle includes a fluid port extending and the delivery catheter extends between a proximal end and a distal end thereof. The proximal end of the delivery catheter is coupled to the handle. The delivery catheter defines a lumen extending along a longitudinal length of the delivery catheter. The medical device is coupled to the distal end of the delivery catheter. Further, the medical device includes a hub and an occluder portion. The hub defines a bore and the occluder portion is coupled to the hub and extends radially and distally from the hub. The occluder portion includes a substantially non-permeable material. With this arrangement, each of the handle, the delivery catheter and the medical device define a common fluid flow path configured to advance the contrast fluid through the fluid port of the handle, along the lumen defined in the delivery catheter, and through the hub of the medical device to exit a distal side of the hub.

In one embodiment, upon the medical device being positioned within the LAA, the fluid flow path is configured to facilitate movement of the contrast fluid into the LAA on a distal side of the medical device to determine a position of the medical device within the LAA with the imaging device.

In another embodiment, the system further includes a sheath having a length extending between a sheath proximal end and a sheath distal end. The sheath defines a sheath lumen extending through the length of the sheath. Further, the sheath includes a sheath fluid port proximate the proximal end of the sheath. In another embodiment, upon the medical device being positioned in the LAA, the sheath fluid port is configured to advance contrast fluid along a sheath flow path defined by the sheath lumen to flow the contrast fluid over the delivery catheter and to exit the distal end of the sheath to view a proximal side of the medical device positioned in the LAA with the imaging device.

In another embodiment, the substantially non-permeable material of the occluder portion is configured to block the contrast fluid from passing through the occluder portion of the medical device and is viewable with the imaging device. In another embodiment, the substantially non-permeable material of the occluder portion includes at least one of foam and ePTFE.

In another embodiment, the medical device includes an anchor portion with engaging members for engaging tissue in the LAA. In still another embodiment, the medical device includes an anchor portion such that the anchor portion is coupled to the occluder portion with a hinge arrangement and such that the anchor portion pivots relative to the occluder portion. In yet another embodiment, the medical device includes an anchor portion such that the anchor portion is moveable between a retracted position and a deployed position upon the occluder portion being in an occluder deployed position. In still another embodiment, the medical device includes an anchor portion extending between a first end and a second end such that the first end is pivotably coupled to the occluder portion and the second end is coupled to an anchor hub actuating member, the anchor hub actuating member being moveable through the hub. In yet another embodiment, the medical device system includes at least one of an imaging member and a sensor coupled to at least one of a sheath and the delivery catheter, the delivery catheter configured to extend through a sheath lumen of the sheath.

In accordance with another embodiment of the present invention, a method for modifying a left atrial appendage ("LAA") of a heart is provided. The method includes: anchoring a medical device in the LAA with a delivery catheter directly coupled to a hub of the medical device such that the medical device includes an occluder material extending over a proximal side of medical device with occluder material flaps adjacent the hub in an open first position; and detaching the catheter from the hub of the medical device such that the occluder material flaps adjacent the hub automatically move to a closed second position to close-off the hub of the medical device.

In one embodiment, the method step of anchoring the medical device includes anchoring the medical device having a spring element positioned over the hub and enveloped at least partially by the occluder material flaps. In another embodiment, the method step of anchoring includes anchoring the medical device with the occluder material being a polymeric material.

In another embodiment, the method step of detaching includes unthreading the catheter from the medical device. In another embodiment, the method step of detaching includes detaching the catheter having threads from a threaded portion of the medical device. In still another embodiment, the method step of detaching includes closing a bore of the hub with the occluder material flaps being biased to the closed position such that the occluder material flaps substantially eliminate exposure of metallic material on the proximal side of the medical device at the hub of the medical device.

In accordance with another embodiment of the present invention, a method for modifying a left atrial appendage ("LAA") of a heart is provided. The method includes: anchoring a medical device in the LAA with a delivery catheter coupled to a hub of the medical device such that the medical device includes a moveable portion positioned adjacent the hub and moveable between an open first position and a closed second position, the moveable portion in the open first position with the delivery catheter coupled to the medical device; and detaching the delivery catheter from the hub of the medical device such that the moveable portion adjacent the hub automatically moves to the closed second position to close-off the hub of the medical device.

In one embodiment, the method step of anchoring includes anchoring the medical device including the moveable portion having a spring element, the spring element biased upon being in the open first position and the spring element relaxed upon being in the closed second position. In another embodiment, the method step of anchoring includes anchoring the medical device including the moveable portion having a spring element adjacent the hub and biased toward a flat configuration.

In accordance with another embodiment of the present invention, a medical device system for modifying a left atrial appendage ("LAA") of a heart is provided. The medical device system includes a delivery catheter and a medical device. The delivery catheter extends between a proximal end and a distal end. The medical device is removeably coupled to the distal end of the catheter. The medical device includes a hub and multiple frame segments extending from the hub. The frame segments include an occluder portion extending over at least a proximal side of the frame segments of the medical device with occluder portion flaps adjacent the hub. With this arrangement, the occluder portion flaps are configured to be positioned in an open first position and a closed second position such that the occluder portion flaps are in the open first position with the delivery catheter coupled to the medical device and the occluder portion flaps are in the closed second position upon the delivery catheter being removed from the medical device.

In one embodiment, in the closed second position, the occluder portion flaps are configured to substantially close-off a bore defined in the hub of the medical device. In another embodiment, in the closed second position, the occluder portion flaps are configured to substantially eliminate exposure of metal on the proximal side of the medical device adjacent the hub.

In another embodiment, the occluder portion flaps include a spring element configured to bias the occluder portion flaps from the open first position to the closed second position. In still another embodiment, the occluder portion flaps include a spring element configured to bias toward a flat configuration. In another embodiment, the occluder portion flaps include a spring element having a clover configuration.

In another embodiment, the occluder portion includes a tissue-growth promoting structure configured to promote endothelization. In still another embodiment, the tissue-growth promoting structure includes a polymeric material. In another embodiment, the occluder portion includes at least one of a polymeric material and a metallic material. In yet another embodiment, the delivery catheter is threadably coupled to the medical device.

In accordance with another embodiment of the present invention, a medical device system for modifying a left atrial appendage ("LAA") of a heart is provided. The medical device system includes a delivery catheter and a medical device. The delivery catheter extends between a proximal end and a distal end. The medical device is removeably coupled to the distal end of the delivery catheter. The medical device includes a hub and multiple frame segments that extend from the hub. The frame segments include an occluder portion extending over at least a proximal side of the frame segments of the medical device with a moveable portion adjacent the hub. The moveable portion is configured to be positioned in an open first position and a closed second position such that the moveable portion is in the open first position with the delivery catheter coupled to the medical device and the moveable portion is in the closed second position upon the delivery catheter being removed from the medical device. With this arrangement, the moveable portion is configured to close-off the hub in the closed second position.

In one embodiment, in the closed second position, the moveable portion is configured to substantially eliminate exposure of metal on the proximal side of the medical device adjacent the hub. In another embodiment, the moveable portion includes a spring element configured to bias the moveable portion from the open first position to the closed second position.

In another embodiment, the occluder portion includes a tissue-growth promoting structure configured to promote endothelization. In another embodiment, the tissue-growth promoting structure includes a polymeric material. In yet another embodiment, the moveable portion includes a tissue-growth promoting structure configured to promote endothelization. In still another embodiment, the occluder portion includes at least one of a polymeric material and a metallic material. In another embodiment, the delivery catheter is threadably coupled to the medical device.

These various embodiments may include other components, features or acts as will be apparent from the detailed description set forth below. Additionally, other embodiments, configurations and processes are set forth below in the detailed description of the invention.

BRIEF DESCRIPTION OF THE SEVERAL VIEWS OF THE DRAWINGS

The foregoing and other advantages of the invention will become apparent upon reading the following detailed description and upon reference to the drawings in which:

FIG. 1 is a perspective view of a medical device and a distal portion of a delivery system, according to one embodiment of the present invention;

FIG. 1A is a partial cross-sectional view of the medical device, taken along section line 1A of FIG. 1, according to another embodiment of the present invention;

FIG. 1B is an enlarged section view of an occluder portion, taken from detail 1B of FIG. 1A, according to another embodiment of the present invention;

FIG. 14A and 14B are simplistic side profile views of another embodiment of a medical device, depicting the medical device in an anchor non-deployed position and an anchor deployed position, respectively, according to the present invention;

FIG. 15 is a top view of the occluder portion and the anchor portion of the medical device of FIGS. 14A and 14B, depicting fame components cut from a flat sheet, according to another embodiment of the present invention;

FIG. 18 is a perspective view of a medical device delivery system, depicting a medical device attached and deployed at a distal end of the delivery system, according to another embodiment of the present invention;

FIG. 18A is a cross-sectional view of section 18A of FIG. 18, depicting a lumen defined in a proximal portion of a catheter of the delivery system, according to another embodiment of the present invention;

FIG. 18B is a cross-sectional view of section 18B of FIG. 18, depicting a sheath lumen of a sheath with the catheter of the delivery system therein, according to another embodiment of the present invention;

DETAILED DESCRIPTION OF THE INVENTION

Figure 2:
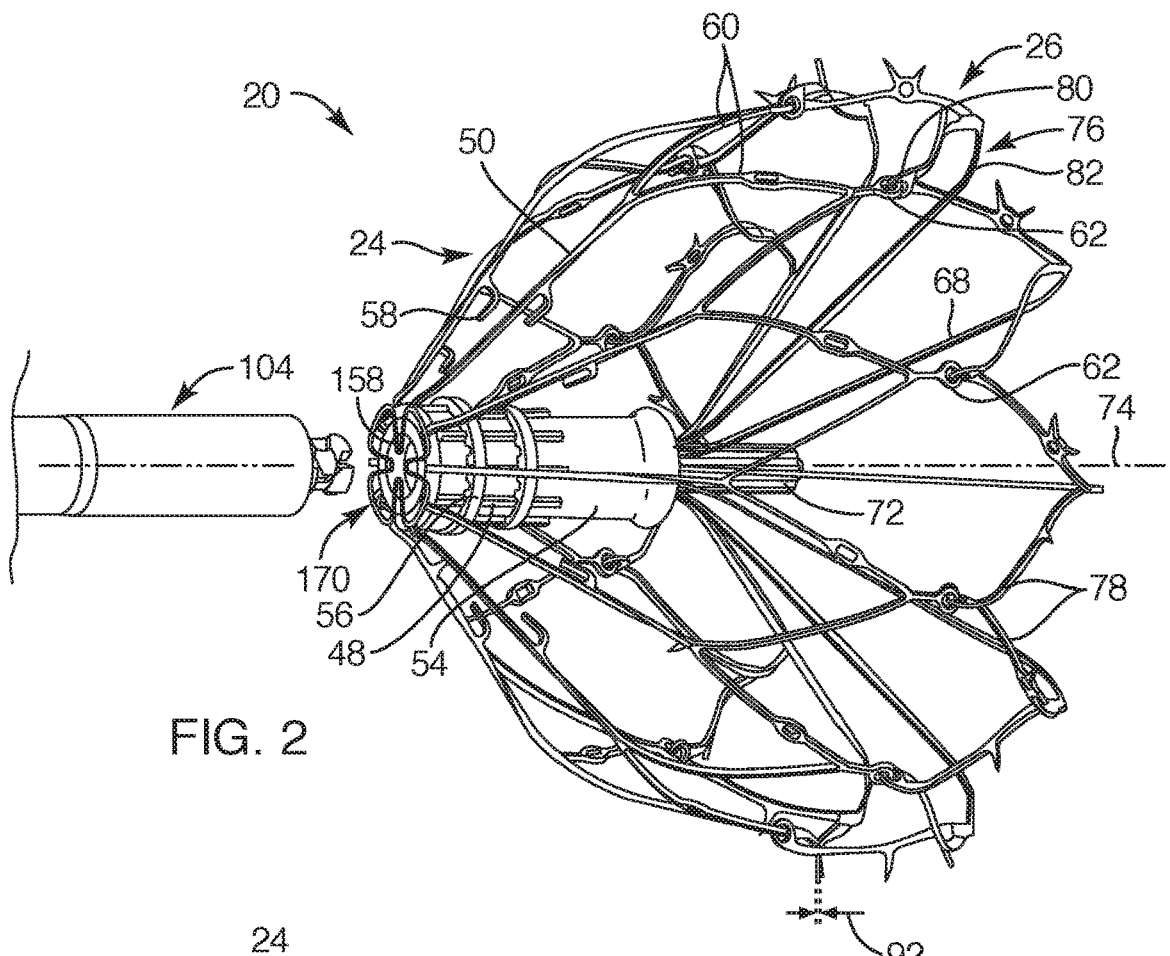
FIG. 2 is a perspective view of the medical device of FIG. 1, depicting the frame without its tissue growth member, according to another embodiment of the present invention.

Referring first to FIGS. 1 and 1A, a medical device 20 and a distal end portion of a delivery system 22 is provided. The medical device 20 and delivery system 22 may be employed in interventional procedures for percutaneously closing and modifying an opening or cavity such as, for example, a left atrial appendage ("LAA") within a heart (not shown). The medical device 20 may include frame components of an occluder portion 24 and an anchor portion 26, the occluder portion 24 also including a tissue growth member 28 attached thereto. Further, the anchor portion 26 may be hingably coupled to the occluder portion 24 such that the anchor portion 26 may be actuated, upon deployment of the occluder portion 24, between a deployed position and a non-deployed position (not shown) via an actuation mechanism at a handle (not shown) of the delivery system 22. With this arrangement, the medical device 20 and delivery system 22 may provide functionality of separating the steps of deploying the occluder portion 24 and the anchor portion 26, thereby, providing additional and enhanced functionality to the physician to properly position and implant the medical device 20 in the LAA.

As set forth, the occluder portion 24 may include an occluder material or a tissue growth member 28 attached thereto. The tissue growth member 28 may be a porous material, or other cell attaching material or substrate, configured to promote endothelization and tissue growth thereover. The tissue growth member 28 may extend over a proximal side of the medical device 20 and, particularly, over the occluder portion 24 and may extend over a portion of the anchor portion 26 and hinges coupling the anchor portion 26 to the occluder portion 24. As such, due to the shape of the frame components of the occluder portion 24, the tissue growth member 28 may include a proximal face that is generally convex to form an outer surface 40. The tissue growth member 28 may also include an inner surface 42 on its distal side that is generally concave shaped. In one embodiment, the tissue growth member 28 may extend primarily over an outside surface of frame components of the occluder portion 24 with a portion of the tissue growth member 28 extending on both the outside surface and the inside surface of the frame components of the occluder portion 24. In another embodiment, the tissue growth member 28 may extend primarily over both the outside surface and the inside surface of the frame components of the occluder portion 24 of the medical device 20. In another embodiment, the tissue growth member 28 may extend solely over the outside surface of the frame components of the occluder portion 24.

With respect to FIGS. 1A and 1B, the tissue growth member 28 may include one or more types of materials and/or layers. In one embodiment, the tissue growth member 28 may include a first material layer 30 and a second material layer 32. The first material layer 30 may primarily be an underside layer or base layer of the tissue growth member 28. The first material layer 30 may include porous and conformable structural characteristics. For example, the first material layer 30 may include a foam type material, such as, a polyurethane foam or any other suitable polymeric material, such as a polymer fabric, woven or knitted. The second material layer 32 may include one or more layers of, for example, an expanded polytetrafluoroethylene (ePTFE) material. The second material layer 32 may be attached to an outer surface of the first material layer 30 with, for example, an adhesive. In one embodiment, the second material layer 32 may include a first layer 32A, a second layer 32B, and a third layer 32C such that the first layer 32A may be directly attached to the first material layer 30 and the third layer 32C may be an outer-most layer covering the proximal side of the medial device 20 with the second layer 32B extending therebetween. The various layers of the second material layer 32 may be bonded together by adhesives and/or by a thermal bonding heat process or other appropriate processes known in the art. In one particular example, the outer-most layers, such as the second and third layers 32B, 32C, may be formed of an ePTFE material having an internodal distance (sometimes referred to as pore size) of approximately 70 μm to approximately 90 μm. The first layer 32A of the second material layer 32, adjacent the first material layer 30, may be formed of an ePTFE material having a reduced internodal distance relative to the second and third layers 32B, 32C. For example, the internodal distance of the first layer 32A may be approximately 10 μm. This first layer 32A may be bonded or adhered to the first material layer 30 using an adhesive material. Any other suitable sized layers of ePTFE may be employed, such as ePTFE having an internodal distance up to about 250 μm. Further, there may be one or more additional layers, similarly sized to the first layer 32A, extending over a hub end 34 with flaps 36 (outlined with an "X" configuration) where the delivery system 22 interconnects with the medical device 20 (see FIG. 1).

The second material layer 32 made of ePTFE effectively prevents the passage of blood, due to the small internodal distance and pore size of the first layer 32A, while the larger internodal distance of other layers (e.g., 32B and 32C) enable tissue in-growth and endothelization to occur. Additionally, the first material layer 30, being formed of a polyurethane foam, enables aggressive growth of tissue from the LAA wall into the tissue growth member 28 at the inside or concave side of the medical device 20. Further, the first material layer 30 provides an exposed shelf 38 on the outer surface 40 around the periphery and distal end portion of the tissue growth member 28, which promotes aggressive fibroblast and tissue growth to further initiate endothelization over the outer surface 40 of the second material layer 32. It is noted that the use of appropriate adhesive materials between the first material layer 30 and the next adjacent layer 32A may also serve to fill in the pores of the next adjacent layer 32A and further inhibit possible flow of blood through the tissue growth member 28. Additional layers of ePTFE may also be included to the second material layer 32 of the tissue growth member 28.

Figure 3:
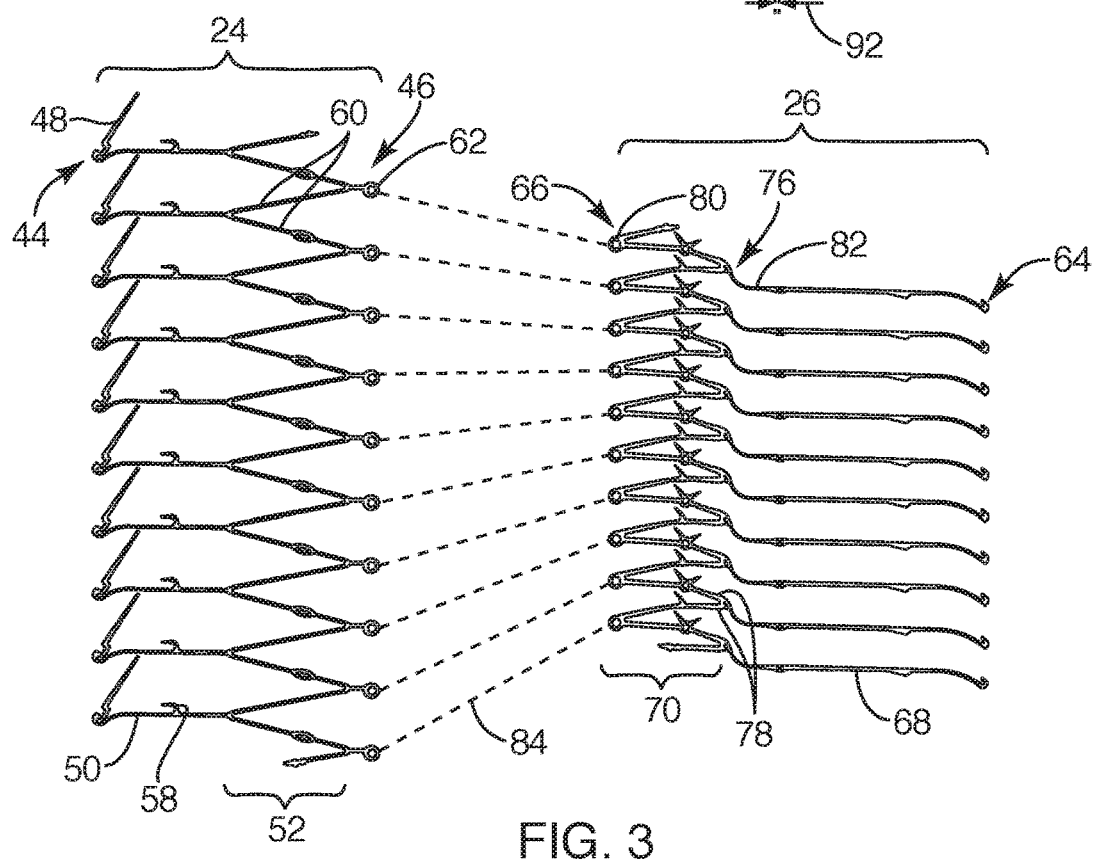
FIG. 3 is a top view of frame components of the occluder portion and the anchor portion of the medical device of FIG. 2, depicting frame components laser cut from a flat sheet prior to being assembled, according to another embodiment of the present invention.

With reference to FIGS. 2 and 3, description of the medical device 20 and its frame components will now be provided. FIG. 2 depicts the frame components in an assembled and fully deployed state and FIG. 3 depicts the frame components as cut from a flat sheet. As previously set forth, the medical device 20 includes an occluder portion 24 and an anchor portion 26. The occluder portion 24 may include multiple occluder frame segments that may be interconnected to form the occluder portion 24. The occluder portion 24 may extend between a first end 44 and a second end 46 with face struts 50 and an occluder zig-zag portion 52 therebetween. Further, the occluder portion 24 includes base extensions 48 extending from the first end 44. The base extensions 48 may be coupled to a hub 54 via rings 56 with notches defined at an inner diameter in the rings 56. Each base extension 48 may extend from a proximal most portion of the occluder portion 24 or first end 44, the first end 44 being one end of each base extension 48 and face strut 50. Each base extension 48 may be sized and configured to be positioned around the hub 54 and held by one or more rings 56. Each base extension 48, at the first end 44, may extend to one face strut 50 of the occluder portion 54, the face strut 50 extending radially and distally from the first end 44. Each face strut 50 may include an extension 58 on a back side thereof, the extension 58 having a hook configuration sized and configured to hold a portion of the tissue growth member (not shown). Further, each face strut 50 extends to a v-extension 60 of the occluder zig-zag portion 52 such that distal ends of each v-extension 60 may be coupled to distal ends of adjacent v-extensions 60 (side-by-side) to define the occluder zig-zag portion 52. The occluder zig-zag portion 52 may enlarge radially and distally from the face struts 50 to a distal end or the second end 46 of the occluder portion 24. At the second end 46, the occluder portion 24 may include an occluder eyelet 62 sized configured to hingably couple to the anchor portion 26.

The anchor portion 26 may include multiple anchor frame segments that may be interconnected to form the anchor portion 26. The anchor portion 26 may extend between a first end 64 and a second end 66 with anchor actuator arms 68 and an anchor zig-zag portion 70 therebetween. The anchor actuator arms 68 may extend between the first end 64 and the anchor zig-zag portion 70. Each anchor actuator arm 68 may be configured to couple to a collar arrangement or splined sleeve 72 at the first end 64 of the anchor portion 26 such that the anchor actuator arms 68 are coupled as a unit or together via the splined sleeve 72. The splined sleeve 72 may be configured to actuate along an axis 74 of the medical device 20 to move the anchor portion 26 between the anchor deployed position and anchor non-deployed position (not shown), discussed in more detail hereafter.

Figure 3A:
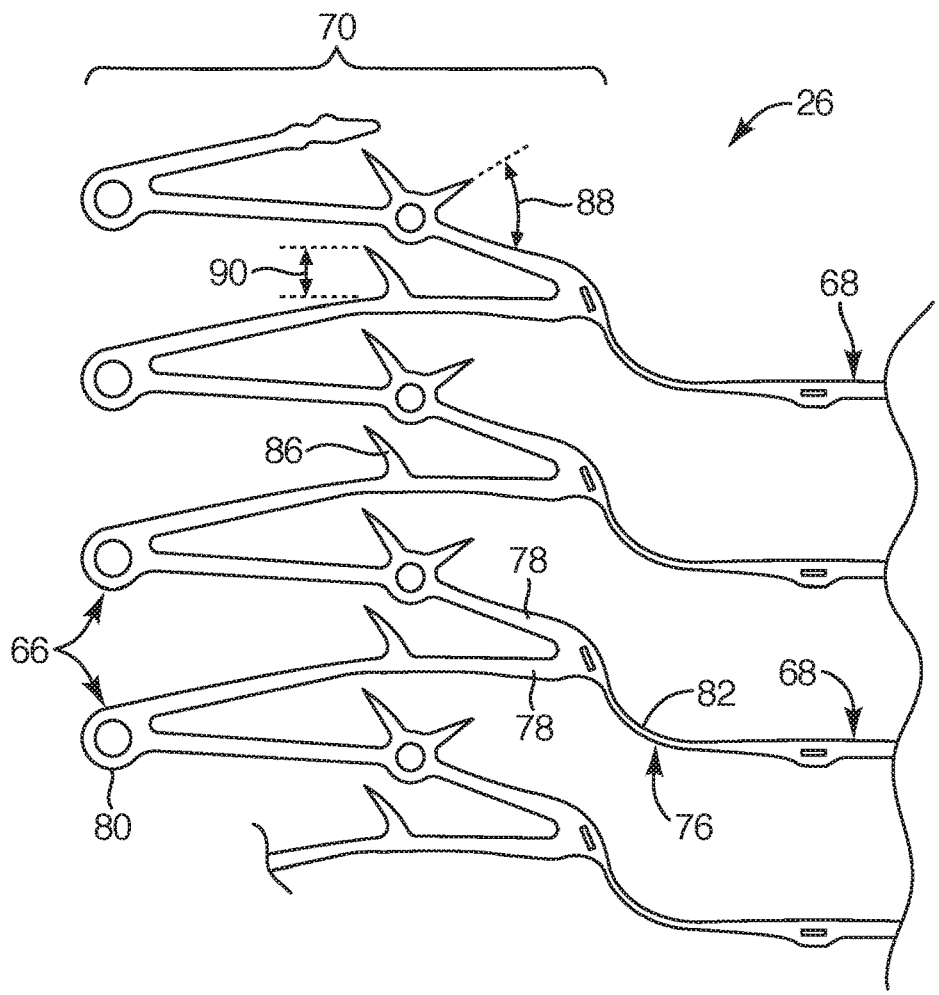
FIG. 3A is a partial enlarged view of the anchor portion depicted in FIG. 3, according to another embodiment of the present invention.

With reference now to FIGS. 2, 3, and 3A, the anchor actuator arms 68 may also include a flexure portion 76. The flexure portion 76 defines a taper 82 and radius extending along the radial length of the flexure portion 76 toward the anchor zig-zag portion 70 and then widens again at the anchor zig-zag portion 70. Such taper 82 along the radial length in the flexure portion 76 facilitates repetitious movement of the anchor portion 26 between the deployed position and the non-deployed position while also maintaining structural integrity of the anchor portion 26, and minimizing the stress and strain in the flexure portion 76 while facilitating a tight radius or loop. In one embodiment, the anchor actuator arms 68 may each include a coil (not shown) that may be wound around a portion of the actuator arm and over the flexure portion 76 with the ends of the coil secured to the anchor actuator arm 68. Such coil may substantially capture the anchor actuator arm 68 from extending in undesirable locations in the LAA should there be a facture or break in the anchor actuator arm 68.

Each flexure portion 76 of the anchor actuator arms 68 may extend to anchor v-extensions 78 such that the proximal ends of each anchor v-extension 78 may be coupled to proximal ends of adjacent anchor v-extensions 78 (similar to the occluder zig-zag portion 52) to form the anchor zig-zag portion 70. At the interconnection of the proximal ends of the anchor v-extensions 78 or the second end 66 of the anchor portion 26, such proximal ends define an anchor eyelet 80. The anchor eyelet 80 may be sized and configured to hingably couple to a corresponding occluder eyelet 62 of the occluder portion 24, as shown by dotted lines 84 (see FIG. 3).

With respect to FIG. 3A, the anchor struts or anchor v-extensions 78 of the anchor zig-zag portion 70 may include one or more hooks 86 or barbs that may extend at an acute angle 88 from the anchor portion 26 or anchor v-extensions and remote from the occluder portion 24. Such acute angle 88 may range between about forty-five degrees and about sixty degrees. Further, the hooks 86 may extend from the anchor v-extensions 78 with a predetermined height 90 so as to provide effective engagement with a tissue wall within the LAA, but not to the extent of piercing all the way through the tissue wall to cause effusions in the LAA. The hooks also include a thickness 92 (see FIG. 2). Such thickness 92 may be similar to the thickness of sheet material from which the fame components (i.e., occluder portion 24 and anchor portion 26) of the medical device 20 are cut.

With respect to FIG. 3, the occluder portion 24 and the anchor portion 26 are depicted in a pre-formed state subsequent to being laser cut from a flat sheet or sheet material of, for example, super elastic material, such as Nitinol. As such, the occluder portion 24 and the anchor portion 26, in the pre-formed state, may be substantially planar and flat, after which, the frame components of the occluder portion 24 and/or the anchor portion 26 may then be heat-set to a desired shape and configuration, as known to one of ordinary skill in the art, similar to the fully deployed configuration (see FIG. 2). Further, as known to one of ordinary skill in the art, other processes may be employed, such as chemical etching and electro-polishing of the frame components. The occluder portion 24 may include ten face struts 50 and ten base extensions 48 with ten occluder eyelets 62 extending from the occluder zig-zag portion 52. Similarly, the anchor portion 26 may include ten anchor actuator arms 68 with ten anchor eyelets 80 extending from the anchor zig-zag portion 70. It should be noted that the occluder portion 24 and anchor portion 26 may include more or less frame components, such as the respective face struts 50 and anchor actuator arms 68, as known to one of ordinary skill in the art. As shown by dotted line 84, occluder eyelets 62 may be configured to couple to corresponding anchor eyelets 80 with a hinge-like coupling arrangement. Such may be employed by directly interlocking the occluder eyelets 62 with the anchor eyelets 80, as depicted in FIG. 2.

In another embodiment, the fame components of the occluder portion 24 and the anchor portion 26 may be laser cut from tubular material, rather than a flat sheet. In this embodiment, the frame components may be laser cut, and then heat set to the desired configuration, similar to that shown in FIG. 2. Various frame components of the occluder portion 24 and the anchor portion 26 may need to be modified as readily understood by one of ordinary skill in the art.

Figure 3B:
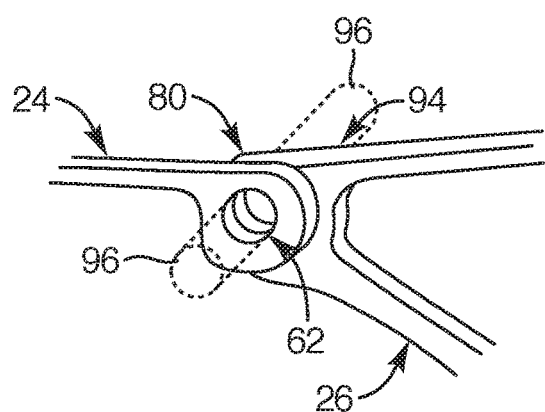
FIG. 3B is an enlarged view of a hinged coupling between the occluder portion and the anchor portion of the medical device, according to another embodiment of the present invention.

With reference to FIG. 3B, in another embodiment, the occluder portion 24 and the anchor portion 26 may be hingably coupled together by aligning the occluder eyelets 62 with the anchor eyelets 80 and positioning an individual interlocking piece 94 (shown in outline) within and through each of the respective aligned eyelets 62, 80. Such an interlocking piece 94 may be a polymeric filament or the like. Ends 96 of the interlocking piece 94 may be heated to form a bulbous shape (not shown) at the ends 96 that, upon cooling, harden and maintain the bulbous shape so as to prevent the respective aligned eyelets from de-coupling. In this manner, the occluder and anchor eyelets 62, 80 may be interlocked via the interlocking piece 94 to provide a hinged coupling arrangement for the anchor portion 26 to pivot relative to the occluder portion 24 and, more particularly, for the anchor portion 26 to pivot about the occluder eyelets 62. In another embodiment, the interlocking piece 94 may be a metallic rivet press fitted through aligned eyelets to provide a hinged coupling arrangement.

Figure 4:
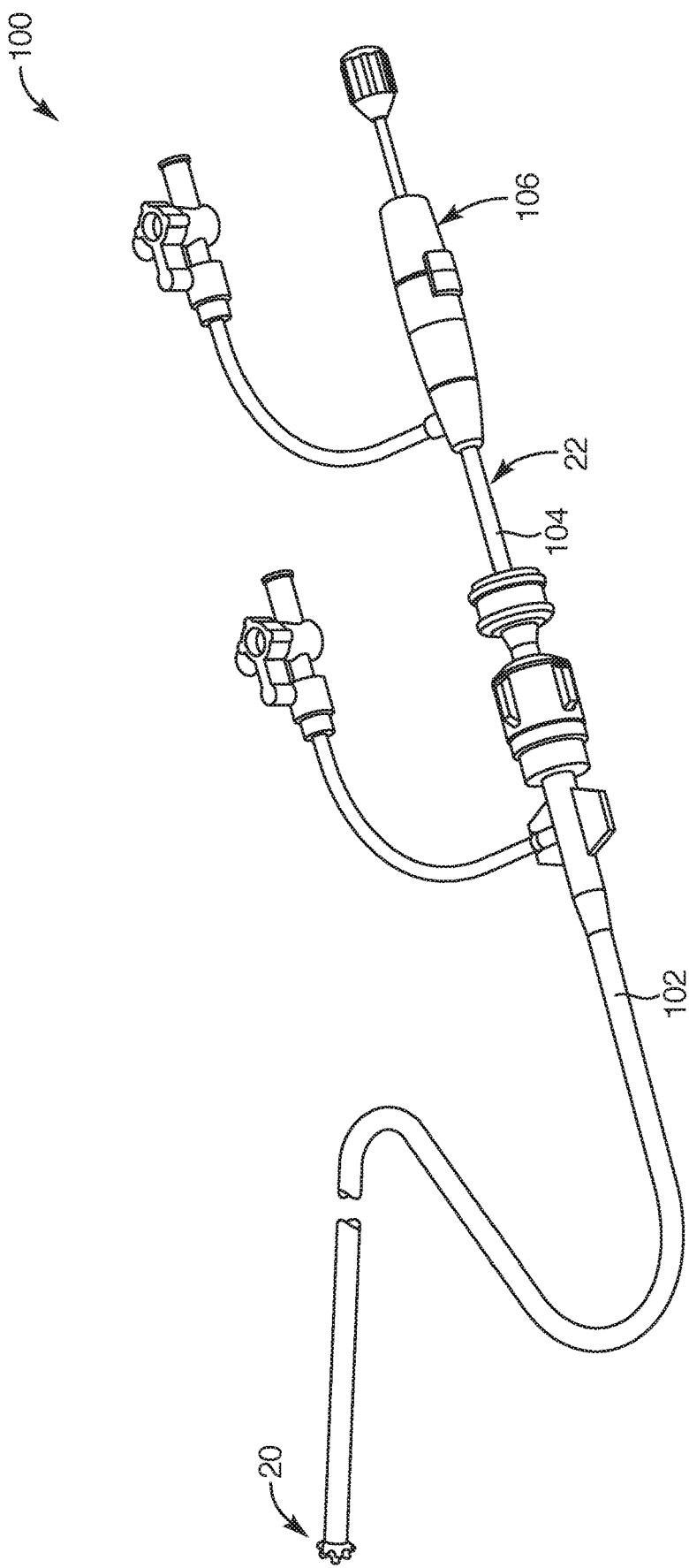
FIG. 4 is a perspective views of a medical device delivery system, according to another embodiment of the present invention.

Now with reference to FIG. 4, a medical device delivery system 100 for delivering the medical device 20 to, for example, the LAA is provided. The medical device delivery system 100 may include the before-mentioned delivery system 22, the medical device 20, and a sheath 102. The delivery system 22 may include a delivery catheter 104 coupled to a handle 106 with the medical device 20 operatively coupled to the handle 106 at a distal end of the delivery catheter 104. The delivery catheter 104 may be sized and configured to be inserted through the sheath 102 such that the medical device 20 may be pushed through the sheath 102 to the distal end thereof. The medical device 20 may be partially exposed, at certain stages of delivery, as depicted. The functionality and detail of the various components of the medical device delivery system 100 will be described in detail hereafter.

Figure 5:
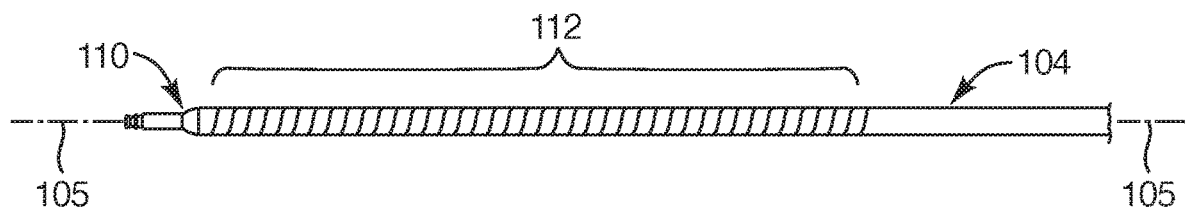
FIG. 5 is a side view of an end portion of a delivery catheter, according to another embodiment of the present invention.
Figure 5A:
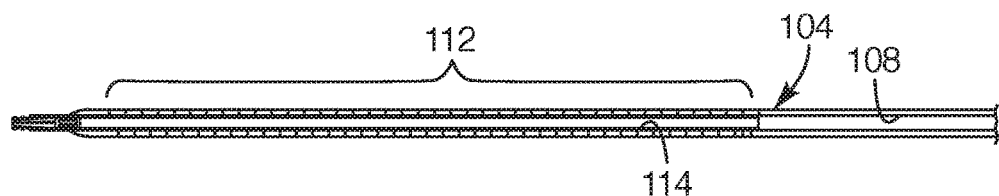
FIG. 5A is a cross-sectional view of the end portion of the delivery catheter, taken along a longitudinal axis of the delivery catheter of FIG. 5, according to another embodiment of the present invention.
Figure 5B:
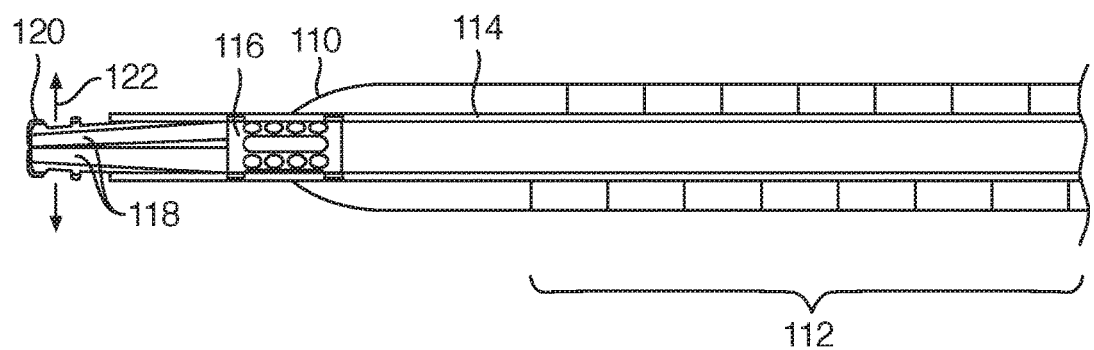
FIG. 5B is an enlarged view of the end portion of the delivery catheter, according to another embodiment of the present invention.

With reference now to FIGS. 5, 5A, and 5B, a distal portion of the delivery catheter 104 will now be described, FIG. 5A being a cross-sectional view of the distal portion of the delivery catheter 104 along an axis 106 thereof depicted in FIG. 5 and FIG. 5B being an enlarged cross-sectional view of a portion of the same. The delivery catheter 104 may define a lumen 108 extending longitudinally therethrough between a proximal end (not shown) and a distal end 110 of the delivery catheter 104. In one embodiment, the delivery catheter 104 may include a shaft (not shown), a spiral cut portion 112, an inner distal tube 114, and a collet 116. Such distal portion of the delivery catheter 104 may include enhanced lateral flexiblity along the region of the spiral cut portion 112. That is, the distal portion of the delivery catheter 104 may be more flexible than portions of the delivery catheter 104 more proximal than the spiral cut portion 112. The spiral cut portion 112 may be formed by spirally or helically cutting a slit into the peripheral structure of the distal portion of the delivery catheter 104, as depicted. The inner distal tube 114 may be coupled to the delivery catheter 104 and within the lumen 108 of the distal portion of the delivery catheter 104. The collet 116 may be positioned and thermally coupled to the distal end 110 of the delivery catheter 104 and within the inner distal tube 114 with collet fingers 118 extending distally therefrom. The collet fingers 118 may be sized and configured to latch to the hub of the medical device (not shown) with nubs 120 or protrusions extending from free ends of the collet fingers 118. The collet fingers 118 are moveable outward, as indicated by arrows 122, and are biased to an inward position as shown. The collet 116 and collet fingers 118 may be made from a metallic material, such as stainless steel or Nitinol, or any other suitable metallic material that can maintain a biasing force. Such inward biasing of the collet fingers 118 will be discussed in further detail hereafter. With respect to the enhanced flexibility of the delivery catheter 104 along the spiral cut portion 112, such enhanced flexibility facilitates the medical device to self-center upon being deployed in the LAA. In other words, the radial strength of the medical device (not shown) may be greater than the lateral forces of the delivery catheter 104 along the spiral cut portion 112 to, thereby, allow the medical device to self-center in the LAA in instances where the axis 106 of delivery catheter cannot be made concentric to the ostium of the LAA during delivery and deployment of the medical device.

Figure 6A:
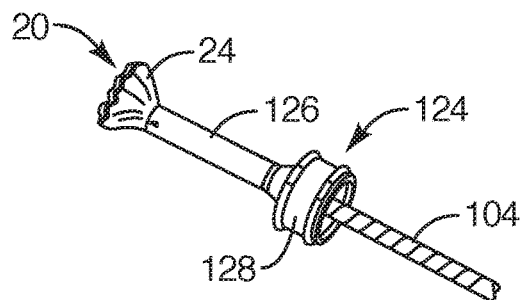
FIGS. 6A-6C are perspective views of a loader, depicting the loader being pushed over an occluder portion of the medical device, the medical device inserted into a sheath, and pushed to a distal end of the sheath, respectively, according to another embodiment of the present invention.
Figure 6B:
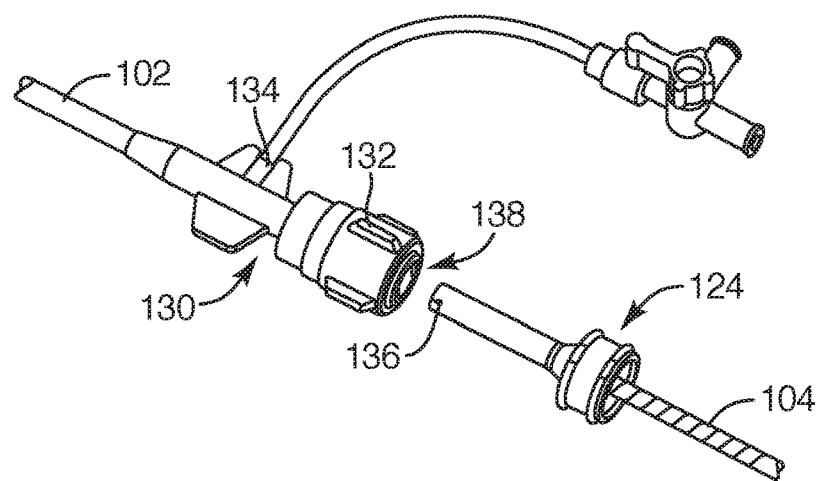
Figure 6C:
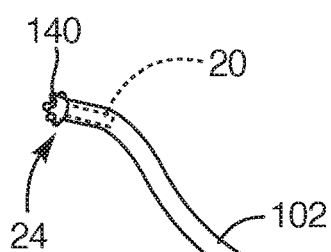
Figure 6C:
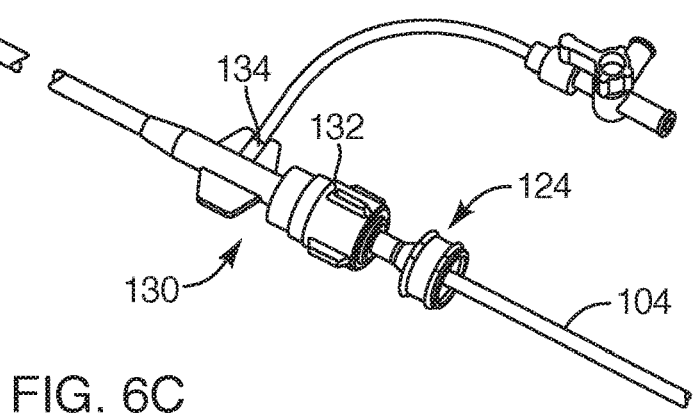
Figure 8:
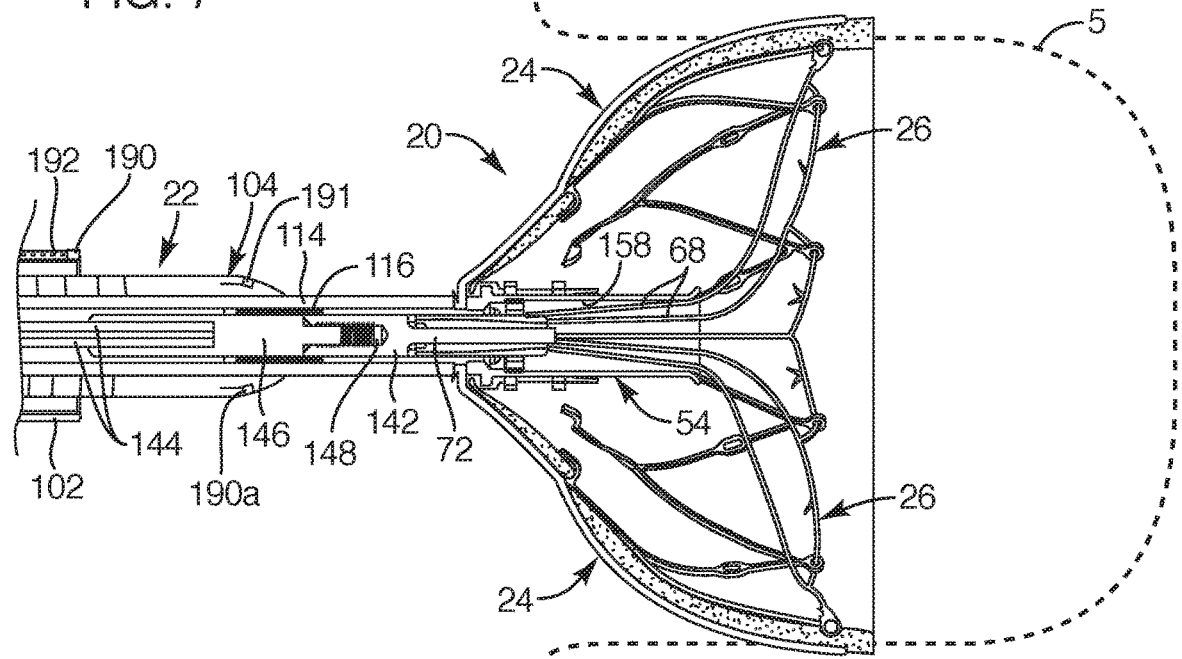
FIG. 8 is a cross-sectional side view of the distal portion of the delivery system and the medical device, depicting a sheath withdrawn to deploy the occluder portion of the medical device in the LAA and depicting the anchor portion in an anchor non-deployed position, according to another embodiment of the present invention.
Figure 8A:
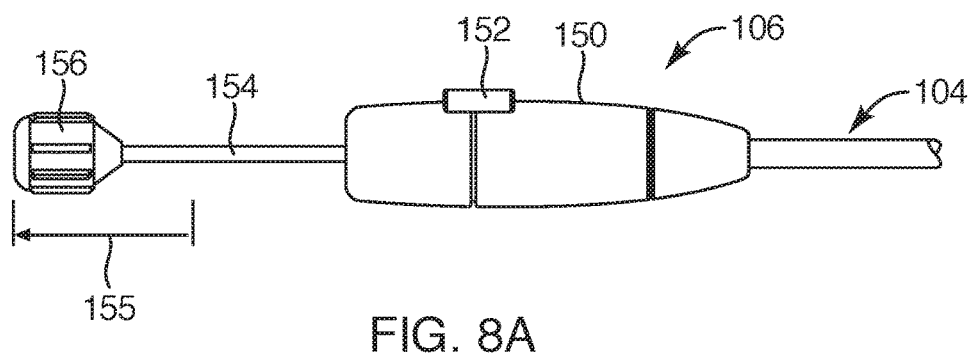
FIG. 8A is a side view of a handle, depicting the handle in a first position corresponding to the anchor non-deployed position, according to another embodiment of the present invention.

Now with reference to FIGS. 6A, 6B, and 6C, description of steps that may be employed for loading the medical device 20 into the sheath 102 will now be provided. For example, the delivery catheter 104 may include a loader 124 sized and configured to facilitate loading the occluder portion 24 of the medical device 20 into the sheath 102 so that the delivery catheter 104 can push the occluder portion 24 through the sheath 102 to a distal portion thereof. With reference to FIG. 6A, the loader 124 may include a tube portion 126 and a handle portion 128. The loader 124 may be slideably positioned over the delivery catheter 104 such that the delivery catheter 104 extends through a bore defined through the loader 124. The loader 124 may be moved over the distal end of the delivery catheter 104 and manually moved or forced over the occluder portion 24 of the medical device 20 so that occluder portion 24 moves to a constricted position enclosed within the tube portion 126. However, prior to moving the loader 124 over the occluder portion 24, the anchor portion should be in a non-deployed position such that an actuator knob and plunger shaft of the handle 106 should be moved to a proximal position, as depicted in FIGS. 8 and 8A. Referring back to FIG. 6A, once the loader 124 is moved completely over the occluder portion 24, the medical device 20 may then be advanced through the sheath 102. The sheath 102, at this point, has already been advanced through the circulatory system to the heart with a distal portion of the sheath 102 positioned in the LAA (not shown), employing typical techniques known in the art.

As depicted in FIGS. 6B and 6C, the loader 124 may be inserted into the sheath 102 and, more particularly, a sheath hub 130. The sheath hub 130 may be coupled at a proximal end of the sheath 102. The components of the sheath hub 130 may include a valve 132 and a sheath fluid port 134. The valve 132 may be a rotating hemostasis valve, such as a Touhy Borst valve or the like, configured to constrict or limit back-flow of blood from the sheath 102 upon rotation of the valve 132. The sheath fluid port 134 may extend from the sheath hub 130 and may be sized and configured to flush or aspirate air from the sheath 102 that may become trapped upon loading the medical device 20 into the sheath 102. In another embodiment, the loader 124 may also include a valve positioned around the delivery catheter 104 to maintain hemostasis while inserted into the sheath hub 130.

As set forth, the loader 124 may be mated or inserted into the sheath hub 130 with a snap or click fit via nubs 136 at the distal end of the tube portion 126 and a rib (not shown) within a bore 138 defined in the sheath hub 130. Once the loader 124 is positioned within the sheath hub 130, the delivery catheter 104 may be advanced through a lumen defined longitudinally in the sheath 102 such that the distal end of the delivery catheter 104 moves to a distal portion of the sheath 102 to expose a distal tip of the occluder portion 24 of the medical device 20 from the distal end of the sheath 102. With this arrangement, the distal tip of the occluder portion 24 may be exposed at the distal end of the sheath 102 and provides, due to the occluder material, a cushioned tip 140, without any exposed metal frame members, facilitating an atraumatic entry into the LAA, thereby, reducing the potential of effusions in the LAA.

Referring to FIGS. 7 through 11, deployment and detachment of the medical device 20 in an LAA 5 (shown in outline) relative to the delivery system 22 will now be described. With respect to FIGS. 7 and 8, upon the physician positioning the distal portion of the sheath 102 in the LAA 5 with the medical device 20 positioned at the distal portion of the sheath 102 with the cushioned tip 140 of the occluder portion 24 exposed at the distal end of the sheath 102, the physician may atraumatically position the distal portion of the sheath 102 to a desired location in the LAA 5. Once the desired location is determined, the physician can deploy the occluder portion 24 of the medical device 20. Such may be employed by simply withdrawing the sheath 102 or manually moving the sheath 102 in a proximal direction. As the sheath 102 is withdrawn, the occluder portion 24 self-expands to an occluder deployed position with the anchor portion 26 maintained in an anchor non-deployed position, as depicted in FIG. 8.

With respect to FIG. 8, a distal portion of the delivery catheter 104 coupled to the medical device 20 is shown. The delivery catheter 104 of this embodiment is coupled to the medical device 20 with an occluder hub nut 142 and collet 116 arrangement. For example, the distal portion of the delivery catheter 104 includes the inner distal tube 114 and an actuator shaft 144. The actuator shaft 144 may include a layered coil, such as a speedometer cable, at a distal end portion thereof, which may be coupled to an inner distal connector 146 moveable within the collet 116. As previously set forth, the collet 116 may include collet fingers 118 extending distally from the collet 116. The inner distal connector 146 may include threads sized and configured to couple to the occluder hub nut 142 and, more particularly, to a threaded screw hole 148 defined in the occluder hub nut 142. The occluder hub nut 142, at a distal end thereof, may include the splined sleeve 72. As previously set forth, the splined sleeve 72 may be sized and configured to couple end portions of each of the anchor actuator arms 68. In another embodiment, the inner distal connector 146 and occluder hub nut 142 may be reversed such that the inner distal connector 146 includes a nut configuration and the occluder hub nut 142 includes a screw configuration. In either case, the medical device 20 may be threadably coupled to the delivery catheter 104.

With reference to FIG. 8A, one embodiment of the handle 106 is depicted. The handle 106 may include a handle housing 150, an anchor actuator release button 152, a plunger shaft 154, and an actuator knob 156. The handle housing 150 may be coupled to a proximal portion of the delivery catheter 104. The plunger shaft 154 and actuator knob 156 is shown in a first position that correlates to the anchor portion 26 being in a non-deployed position (see FIG. 8). The plunger shaft 154 and actuator knob 156 may be moved bi-linearly between a first position and a second position while depressing the anchor actuator release button 152. The functions and various components of the handle 106 will become apparent to one of ordinary skill in the art as discussed in further detail hereafter.

As depicted in FIGS. 8 and 8A, the anchor portion 26 of the medical device 20 is in an anchor non-deployed position. The actuator knob 156 and plunger shaft 154 are moved to the first position, as indicated by arrow 155 that corresponds to the anchor non-deployed position prior to loading the medical device 20 into the loader 124 and then into the sheath 102 (see FIGS. 6A and 6B). In the anchor non-deployed position, the inner distal connector 146 is threadably coupled to the occluder hub nut 142 and is positioned proximal the hub 54 with the anchor portion 26 in a first position or an anchors non-deployed position or, otherwise said, an anchors-in position with a portion of the anchor actuator arms 68 proximal the hub 54 and within a bore 158 defined in the hub 54. Further, in the anchor non-deployed position, the plunger shaft 154 and knob 156 of the handle 106 may be in a proximal or first position as well. With this arrangement, a physician may determine the most favorable position of the medical device 20 within the LAA 5 with the occluder portion 24 in the deployed position prior to deploying the anchor portion 26.

Figure 9:
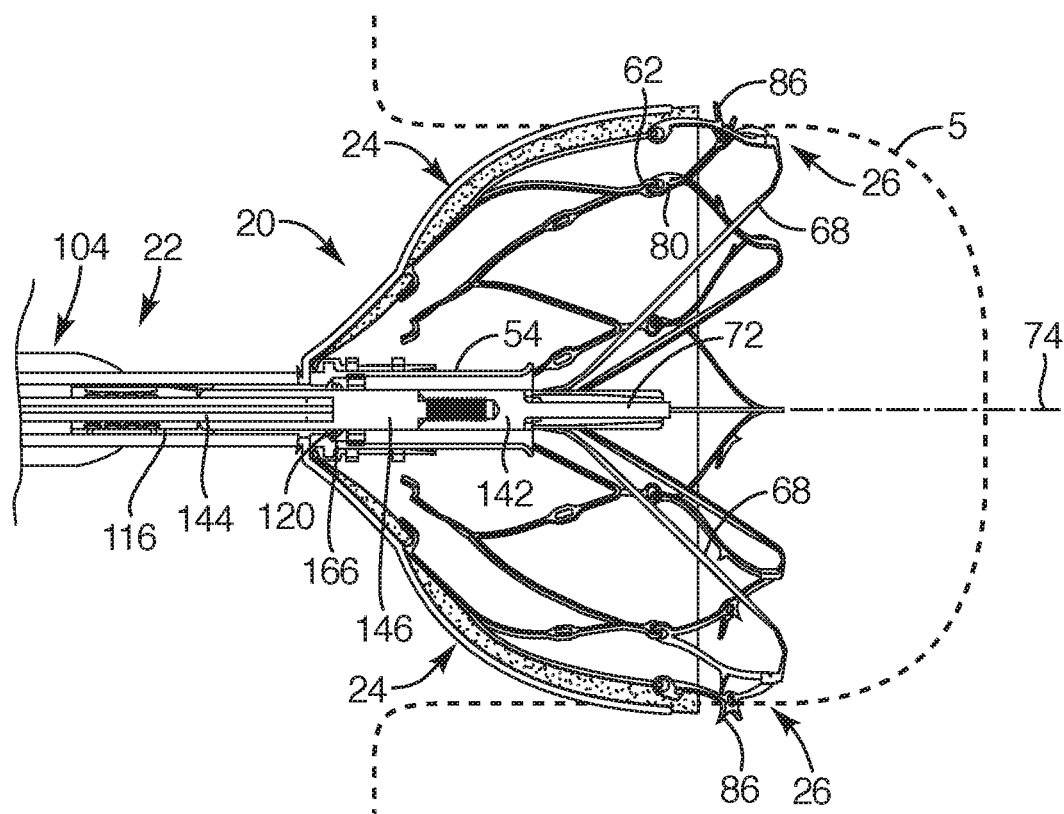
FIG. 9 is a cross-sectional side view of the distal portion of the delivery system and the medical device, depicting both the occluder portion and the anchor portion in an anchor deployed position in the LAA, according to another embodiment of the present invention.
Figure 9A:
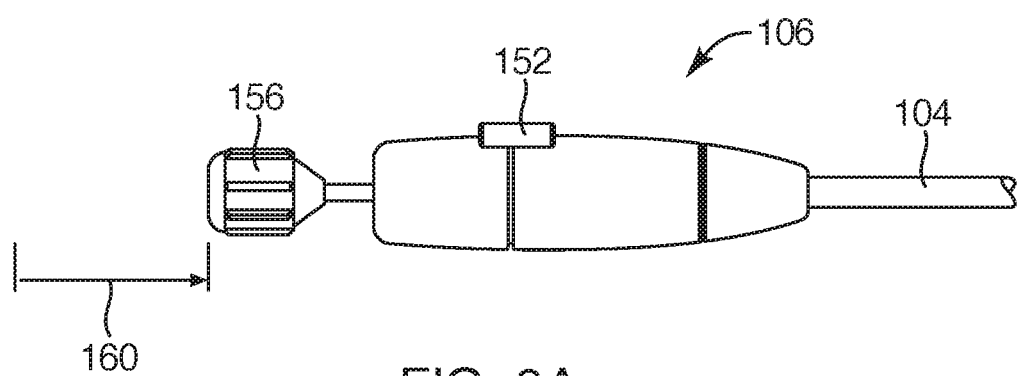
FIG. 9A is a side view of the handle, depicting the handle in a second position corresponding to the anchor deployed position, according to another embodiment of the present invention.

Now turning to FIGS. 9 and 9A, the anchor portion 26 of the medical device 20 may be moved to an anchor deployed position or anchor-out or anchor second position once the physician determines the deployed occluder portion 24 is positioned in the LAA 5 as desired. Such anchor deployed position may be employed by manually moving the actuator knob 156 distally, as indicated by arrow 160, while also depressing the release button 152. In the anchor deployed position, the inner distal connector 146 and occluder hub nut 142 are also moved distally from the collet 116 and into the hub 54 or through the hub 54. Such linear distal movement also moves the anchor actuator arms 68, coupled to the splined sleeve 72, from a distal portion of the delivery catheter 104, through and out of the hub 54 to an everted, deployed position or an expanded position such that the anchor portion 26 unfolds and expands radially by pivoting or rotating at the hinged connection (i.e., at occluder and anchor eyelets 62, 80) between the occluder portion 24 and anchor portion 26. At the anchor deployed position, hooks 86 or tines of the anchor portion 26 are sized and configured to grab tissue and prevent movement so as to effectively anchor the medical device 20 within the LAA 5. Once the anchor portion 26 is deployed, the physician may view the medical device 20 through imaging techniques to ensure proper positioning of the medical device 20 in the LAA 5 while also performing stability tests by pulling proximally on the handle 106 to ensure the medical device 20 is effectively engaging the LAA 5. Such imaging techniques may be enhanced by markers strategically located on the medical device 20 and delivery catheter 104 to provide imaging information to the physician. Such markers may be made from a radiopaque material, such as platinum, gold, tantalum, or alloys thereof, or any other suitable radiopaque materials that are biocompatible.

The hooks 86 of the anchor portion 26 may extend both distally and proximally so as to substantially prevent movement of the medical device 20 in both the proximal and distal directions relative to the LAA 5. In one embodiment, the hooks 86 may include an acute angle 88 (FIG. 3A) relative to the axis 74 of the medical device 20 or the struts of the anchor zig-zag portion 70. The hooks 86 are configured to grab and may dig at the tissue of the LAA 5. Such hooks 86 may be sized, oriented, and configured to prevent puncture or piercing of the hooks 86 all the way through the tissue of the LAA 5, but provide effective and even aggressive engagement with the tissue to provide safe anchoring of the medical device 20 in the LAA 5.

If the physician is dissatisfied with the location or engagement of the medical device in the LAA, the physician may readily disengage the anchor portion 26 from the tissue of the LAA by simply moving the actuator knob 156 in the proximal direction to the first position (FIG. 8A), which simultaneously moves the actuator shaft 144 proximally and, thus, pivots the anchor portion 26 to a disengaged or anchor non-deployed position. The physician may then re-position the occluder portion 24 within the LAA 5 and, once satisfied with the location of the occluder portion 24 in the LAA 5, the physician may readily move the actuator knob 156 forward or a distal direction to pivot and re-engage the anchor portion 26 with the tissue of the LAA 5. The physician may then determine again through imaging and stability tests if the medical device 20 is positioned in the LAA 5 in an effective and safe manner that satisfies the physician. As can be readily understood, the steps of re-positioning the occluder portion 24 and re-engaging the anchor portion 26 of the medical device 20 can be repeated until the physician is satisfied.

Figure 10:
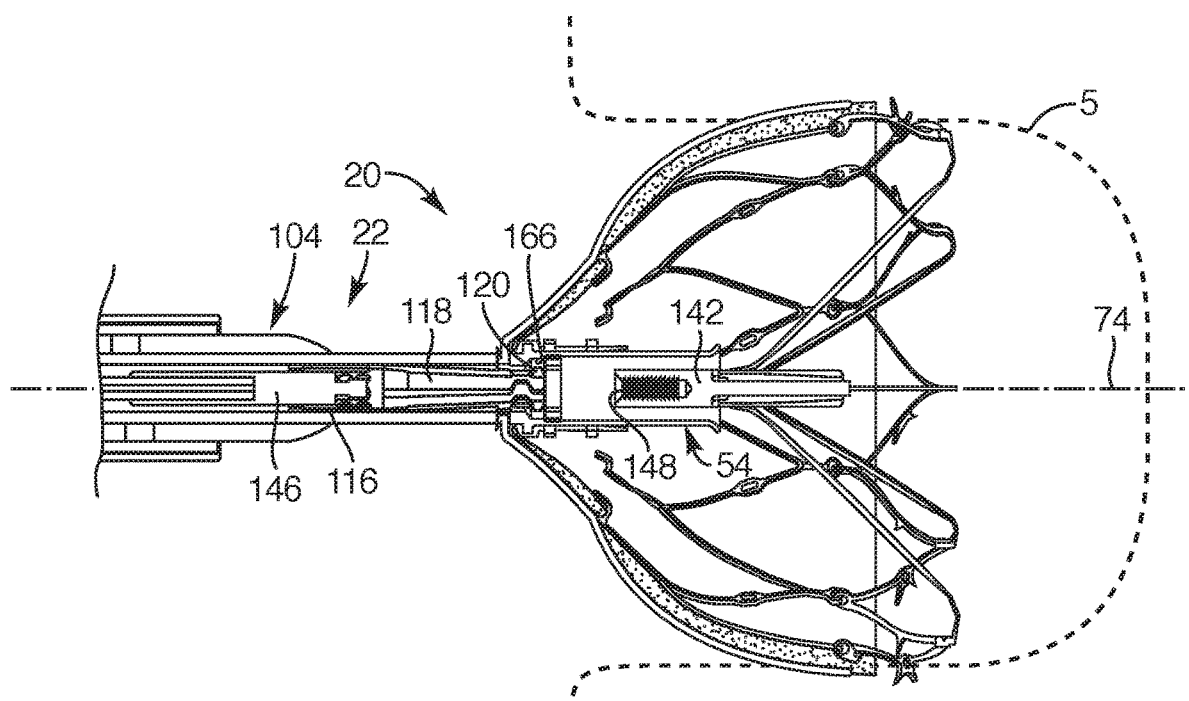
FIG. 10 is a cross-sectional side view of the distal portion of the delivery system and the medical device, depicting the delivery system in the process of being released from the medical device in the LAA, according to another embodiment of the present invention.
Figure 10A:
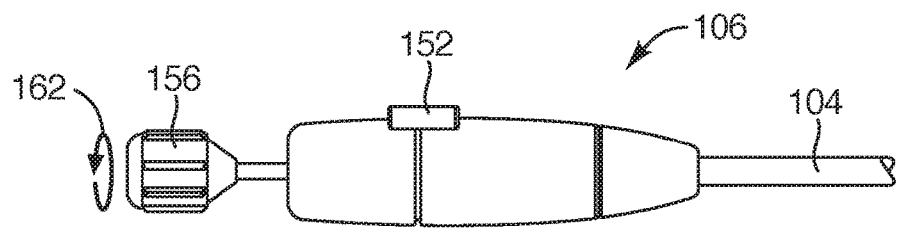
FIG. 10A is a side view of the handle, depicting a portion of the handle being rotated for releasing the medical device, according to an embodiment of the present invention.
Figure 10B:
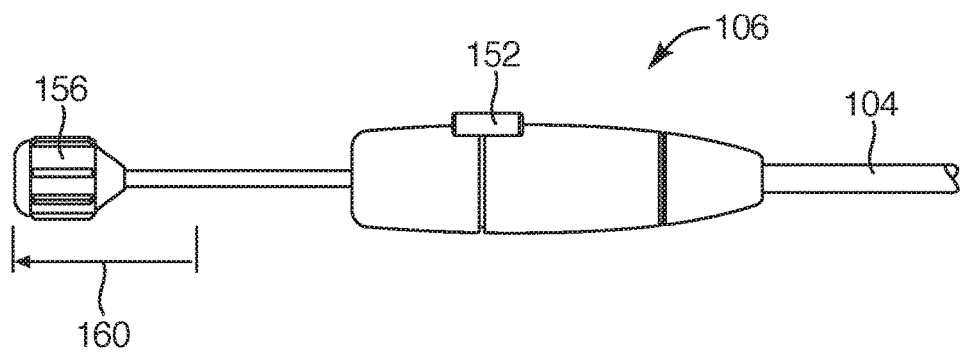
FIG. 10B is a side view of the handle, depicting a portion of the handle actuated from the second position to the first position, according to an embodiment of the present invention.
Figure 11:
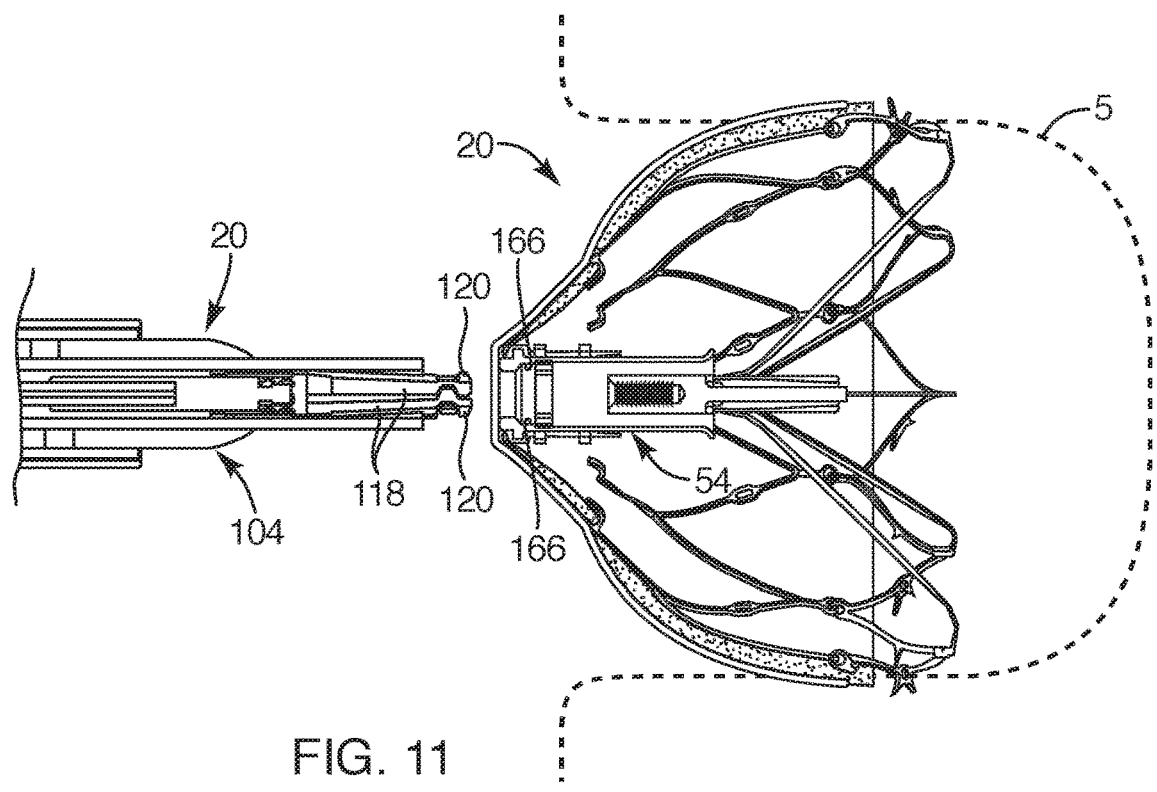
FIG. 11 is a cross-sectional side view of the distal portion of the delivery system and the medical device, depicting the delivery catheter fully released from the medical device, according to another embodiment of the present invention.

Now referring to FIGS. 10, 10A, and 10B, the functions of releasing the medical device 20 will now be described. The medical device 20 may be detached or released by unscrewing the inner distal connector 146 from the screw hole 148 defined in the occluder hub nut 142. Such releasing may be employed by rotating the actuator knob 156 of the handle 106 counter-clockwise several turns, as indicated by arrow 162, until the inner distal connector 146 unwinds from the screw hole 148 of the occluder hub nut 142. The actuator knob 156 may then be pulled proximally back to the first position, as indicated by arrow 164, while depressing the release button 152, which facilitates movement of the inner distal connector 146 in the proximal direction. As the inner distal connector 146 is moved proximally through or into the collet 116, the collet fingers 118 extending distally from the collet 116 collapse inward since the collet fingers 118 may be biased toward an inward position. In other words, prior to the inner distal connector 146 being unwound, the collet fingers 118 may be held in an outer position substantially concentric with the axis 74 of the medical device 20, which maintains the delivery catheter 104 locked to the medical device 20. The collet fingers 118 include outward extending nubs 120 that are held against an abutment 166 within the hub 54 (also shown in FIG. 9). In this manner, once the inner distal connector 146 is unscrewed from the occluder hub nut 142 and moved to a proximal position away from the collet fingers 118, the collet fingers 118 flexibly collapse with a bias to an inward position to move the nubs 120 away from the abutment 166 in the hub 54, thereby, unlocking or unlatching the delivery catheter 104 from the medical device 20. The delivery catheter 104 may then be removed from the medical device 20 with the collet fingers 118 collapsed and the nubs 120 moved proximally from the abutment 166 within the hub 54 as depicted in FIG. 11.

Figure 12:
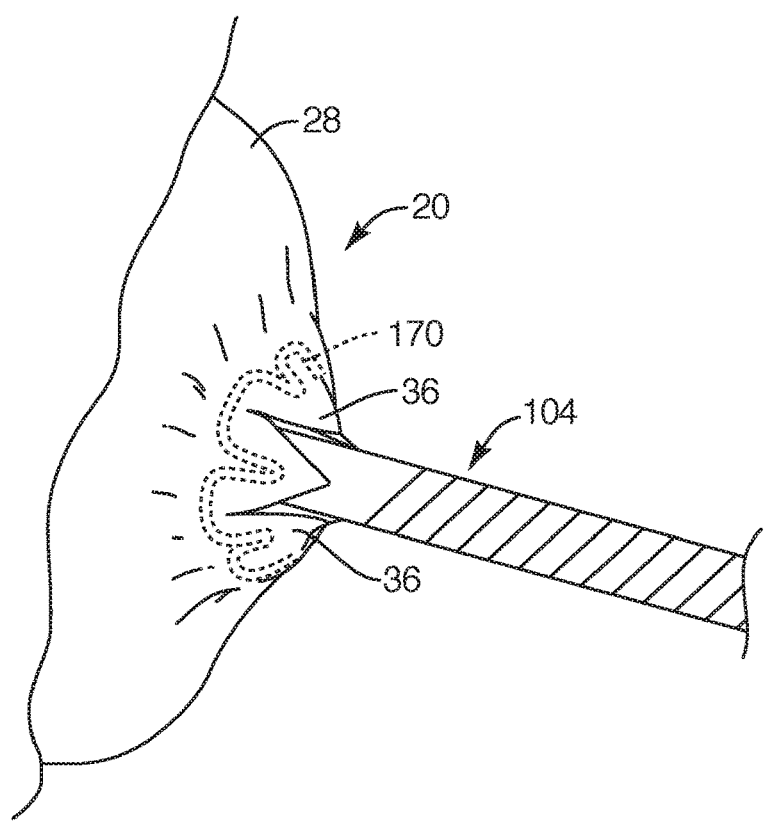
FIG. 12 is a partial perspective view of the proximal side of the medical device coupled to the delivery system, according to another embodiment of the present invention.

With respect to FIGS. 2 and 12, a moveable portion that may include a spring 170 is depicted. In one embodiment, the moveable portion may include a spring 170 with a polymeric covering in the form of polymeric flaps or occluder flaps 36. Such moveable portion having the spring 170 may be sized and configured to close-off the bore 158 of the hub 54 once the delivery catheter 104 is released from the medical device 20. The spring 170 may include a clover configuration or any other suitable configuration to effectively close-off the hub 54. The spring 170 may move between a first biased position (or open first position) and a second relaxed position (or closed second position). The first biased position of the spring 170 (shown in outline form) is depicted in FIG. 12, which is the position of the spring 170 with the delivery catheter 104 coupled to the hub 54. In one embodiment, the position of the delivery catheter 104 attached to the hub 54 holds the spring 170 in the biased or open first position. Once the delivery catheter 104 is removed from the hub 54, the spring 170 may automatically move to the closed, second relaxed position (see FIG. 2) with the occluder flaps 36 (see also FIG. 1) substantially minimizing or eliminating any through hole on the proximal face and adjacent the hub 54. In the second relaxed position of the spring 170, the bore 158 defined in the hub 54 is substantially closed-off with occluder flaps 36, leaving only a cross-like slit (as depicted by adjacently extending occluder flaps 36 in FIG. 1) and substantially eliminating any metal exposed at the hub 54. In this manner, the occluder flaps 36, in the closed second position, advantageously provides a surface at the proximal face of the device without exposed metal at the hub 54 and, further, provides a contiguous surface with the polymeric material of the occluder portion that closes-off the hub 54.

As previously set forth, the spring 170 may be embedded in the occluder material or tissue growth member 28 or attached to an inner occluder material surface such that the spring 170 may include various layers and/or folds of, for example, ePTFE, with one or more slits defining the flaps 36 that facilitates interconnection of the delivery catheter 104 to the hub 54 when the spring 170 is in the first biased position but then may substantially close-off the bore 158 defined in the hub 54 when in the second relaxed position. Such arrangement is advantageous to substantially prevent blood flow through the hub 54 or to substantially prevent the potential of migrating emboli or thrombus from the hub 54 itself once the medical device 20 is positioned in the LAA. In this manner, the spring 170 facilitates closing-off the through hole of the hub 54 and/or covers any exposed metal at the hub so that emboli or thrombus that may collect on the metal is prevented from escaping from the hub. In other words, the flaps 36 provide a substantially impassible barrier relative to otherwise potential migrating emboli or thrombus at the hub 54.

Figure 13A:
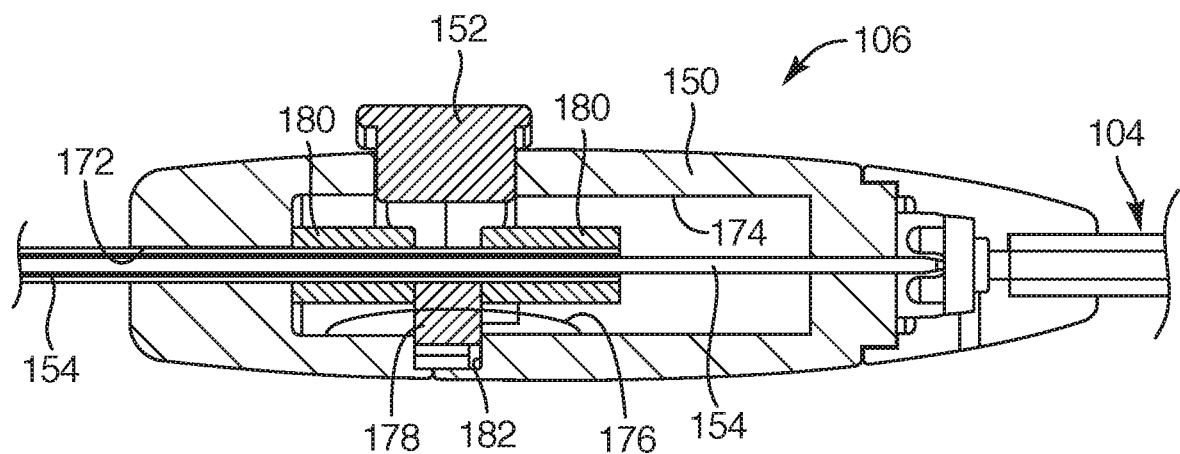
FIGS. 13A and 13B are cross-sectional side views of the handle, depicting a release button in a first and second position, respectively, to facilitate actuation of a plunger shaft, according to another embodiment of the present invention.
Figure 13B:
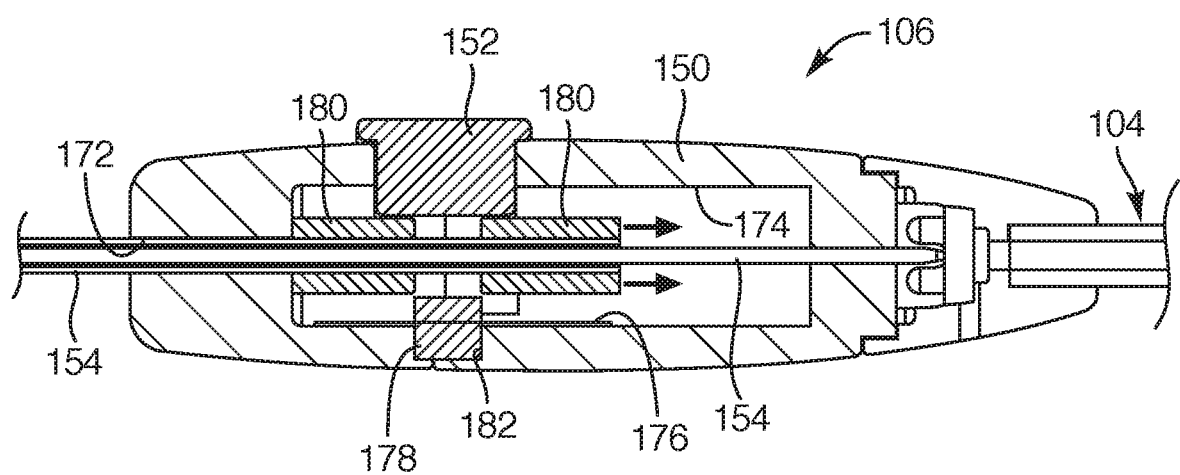

Now referring to FIGS. 13A and 13B, actuation of the release button 152 of the handle 106 is depicted. The handle housing 150 defines a hole 172 that may extend along a longitudinal axis of the handle housing 150 and may be sized to hold the plunger shaft 154 to move bi-linearly therethrough. The handle housing 150 may also define a hollow portion 174 therein. The plunger shaft 154 may extend through the handle housing 150 and be coupled to components coupled to actuator shaft 144 and the inner distal connector 146 at the distal portion of the delivery catheter 104 (see FIG. 9). The handle 106 also may include a leaf spring 176 configured to bias against the release button 152. The release button 152 may include a button post 178. The leaf spring 176 may be coupled to the button post 178 to bias the release button 152 to a non-depressed position or first position. The plunger shaft 154 may also include two travel stops 180 fixed thereto. By depressing the release button 152 to a depressed position or second position, the button post 178 depresses the leaf spring 176 and moves within a cavity 182. Once the button post 178 is moved within the cavity 182, the travel stops 180 coupled to the plunger shaft 154 may then freely move distally (and then back proximally) past the button post 178 a predetermined distance gauged by the travel stops 180 within the hollow portion 174 defined by the handle housing 150. In this manner, the plunger shaft 154 may move the predetermined distance which directly corresponds with the distance or length moved by the actuator shaft 144 and actuation of the anchor portion of the medical device 20 between the anchor non-deployed position and anchor deployed position (see FIGS. 8 and 9).

Referring back to FIG. 8, in another embodiment, the sheath 102 may include an imaging device 190. The imaging device 190 may be sized and configured to be positioned at a distal end of the sheath 102 and may include one or more lines 192 extending from the imaging device 190 and proximally toward the sheath hub 130 (FIG. 5C) for transferring imaging information from the imaging device 190 to a computer and a display (not shown), as known to one of ordinary skill in the art, and viewable by the physician in real-time. The sheath 102, upon being withdrawn from the occluder portion 24, being positioned substantially concentric or proximal of the medical device 20, may be at a vantage point and location in the left atrium adjacent the LAA to provide detailed imaging information otherwise not readily available to the physician. The imaging device 190 may be an ultrasound imaging device or any other suitable imaging device known in the art. In another embodiment, an imaging device 190a may be positioned proximal a distal end of the delivery catheter 104 in a similar manner to that described above. In still another embodiment, the distal end of the delivery catheter 104 and/or sheath 102 may include one or more sensor devices 191. The sensor devices 191 may be configured to sense pressure, flow, and any other cardiac dynamics that may be useful to the physician. In this manner, the sensor devices 191 and/or imaging device 190, 190a may provide additional information to assist the physician to accurately position the medical device 20 in the LAA 5.

Now with reference to FIGS. 14A and 14B, another embodiment of a medical device 200 coupled to a distal portion of a delivery catheter 202, the medical device 200 (depicted in a simplistic profile view) in a partially deployed position and fully deployed position, respectively, is provided. As in previous embodiments, the medical device 200 may include an occluder portion 204 and an anchor portion 206 that may be separately deployed. For example, once a sheath 208 is positioned in the LAA (not shown) with the medical device 200 at a distal end portion thereof, the sheath 208 is withdrawn to deploy an occluder portion 204 of the medical device 200 or to partially deploy the medical device 200. Once the occluder portion 204 is deployed, then the anchor portion 206 may be deployed, to fully deploy the medical device 200.

In this embodiment, the occluder portion 204 is substantially similar to the previous embodiment, except the tissue growth member 210 is attached to an outer surface of the frame components of the occluder portion 204. The tissue growth member 210 of this embodiment may include similar layering of one or more materials as set forth for the tissue growth member described in detail relative to FIG. 1B. Further, although the anchor portion 206 may be hingably coupled to the occluder portion 204 with a hinge arrangement 212 and, in many respects functions similar to the previous embodiment, the anchor portion 206 of this embodiment includes multiple separate and distinct anchor frame segments 214, best shown in FIG. 15.

With reference to FIG. 15, the frame components of the occluder portion 204 and the anchor portion 206 are depicted in, for example, a preformed state subsequent to being laser cut from a flat sheet of super elastic material, such as Nitinol. For simplicity purposes, there is only one anchor frame segment 214 shown, but in this embodiment, there may be five anchor frame segments 214 to correspond and couple to, for example, occluder frame apertures 216 of the occluder portion 204. As shown, the frame components of the occluder portion 204 may be substantially similar to the frame components of the occluder portion 204 described in the previous embodiment relative to FIG. 3.

With respect to the anchor frame segments 214, each anchor frame segment 214 may extend between a first end 218 and second end 220 with two actuator arms 222 extending therebetween such that each anchor frame segment 214 may exhibit a "Y" or "V" configuration in the pre-formed state. Each actuator arm 222 may include an anchor hinge aperture 224 at the second end 220 and, at the first end 218, the actuator arm 222 may be coupled to a collar arrangement 226 or splined sleeve, similar to that of the previous embodiment. With this arrangement, the actuator arms 222, as depicted in FIGS. 14A and 14B, may pivot about the occluder portion 204 at the hinge arrangement 212. Further, the actuator arms 222 may form a loop configuration or loop extension in the anchor deployed position with the first end 218 of the actuator aims 222 moveable or actuatable through the hub 228 of the medical device 200.

Figure 7:
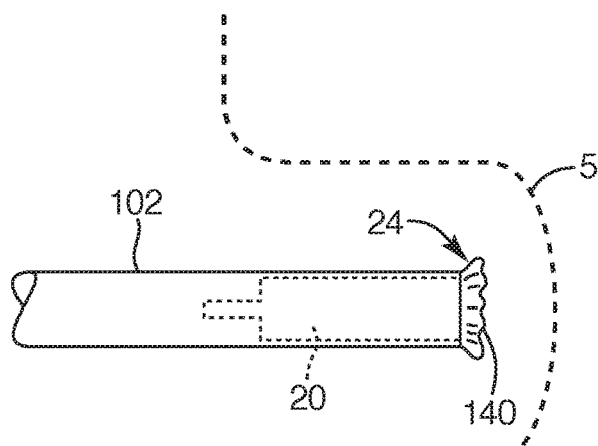
FIG. 7 is a side view of a distal portion of the sheath, depicting a portion of the medical device exposed at a distal end of the sheath in the LAA, according to another embodiment of the present invention.
Figure 16A:
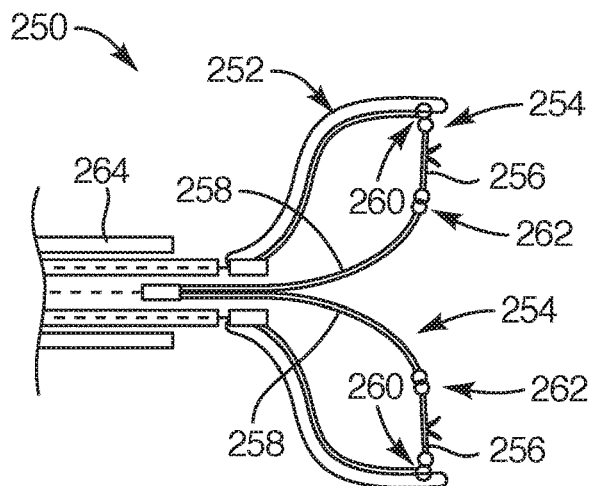
FIGS. 16A and 16B are simplistic side profile views of another embodiment of a medical device, depicting the medical device in an anchor non-deployed position and an anchor deployed position, respectively, according to the present invention.
Figure 16B:
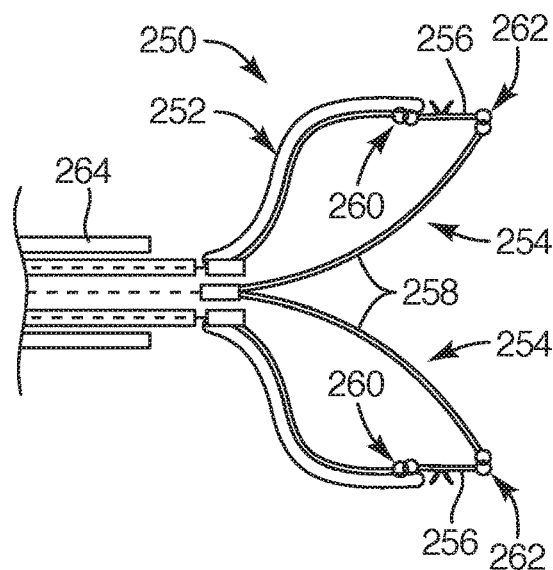
Figure 17:
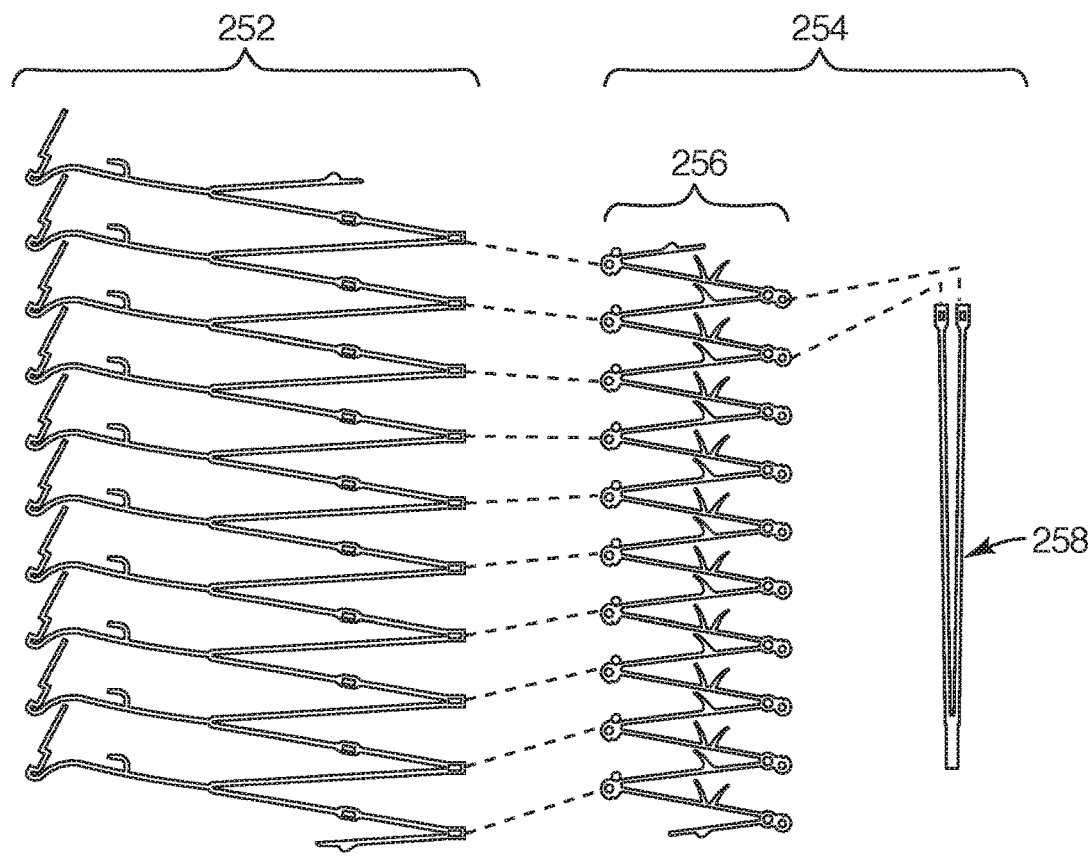
FIG. 17 is a top view of the occluder portion and the anchor portion of the medical device of FIGS. 15A and 15B, depicting frame components cut from a flat sheet, according to another embodiment of the present invention.

Now with reference to FIGS. 16A, 16B, and 17, another embodiment of a medical device 250 depicted in a partially deployed position (FIG. 16A) and a fully deployed position (FIG. 16B), similar to previous embodiments, is depicted. In this embodiment, the occluder portion 252 can be similar to the previous embodiments, but the anchor portion 254 may include an anchor zig-zag portion 256 and loop extensions 258 or actuator arms as separate anchor frame components. In this embodiment, the medical device 250 may include a dual hinge arrangement. For example, the occluder portion 252 may be hingably coupled to an anchor zig-zag portion 256 with a first hinge arrangement 260 and the anchor zig-zag portion 256 may be hingably coupled to the loop extensions 258 with a second hinge arrangement 262. The profile and functionality of the medical device 250 may be similar to the previous embodiments, except the loop extensions 258 may take a more direct inward angle from the anchor zig-zag portion 256 due to the second hinge arrangement 262 therebetween. Similar to the embodiment of FIG. 15, this embodiment may include ten loop extensions 258 or actuator arms, though for simplicity purposes only two loop extensions 258 (as a single loop extension segment) are shown in FIG. 17. It should be noted that the embodiments of FIGS. 14 and 16 also provide the feature to facilitate a cushion tip (not shown) as depicted in FIG. 7 when constricted in the sheath 264. Further, it should be noted the embodiments depicted and described relative to FIGS. 1, 14 and 16 include similar features and structure and, therefore, the descriptions provided in one embodiment may also be applicable to the other described embodiments.

Figure 19:
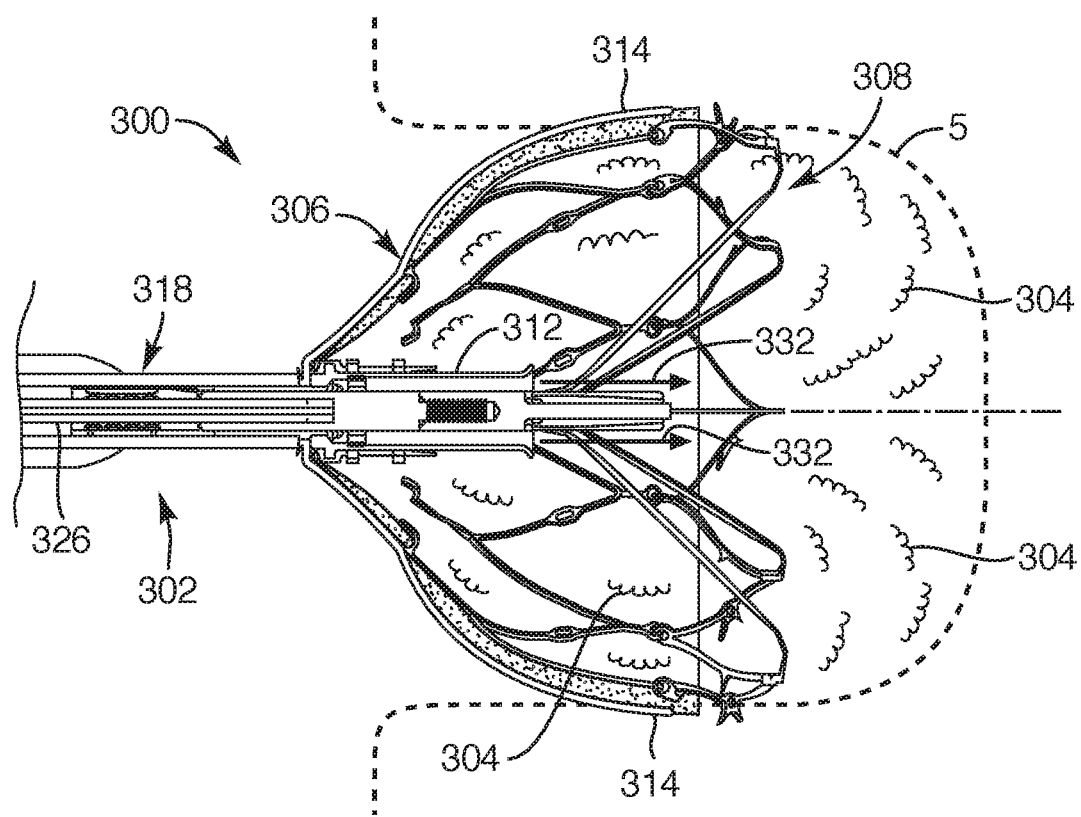
FIG. 19 is a cross-sectional view of the medical device and the distal portion of the delivery system, depicting a contrast fluid flowing from a hub of the medical device and into the left atrial appendage, according to another embodiment of the present invention.
Figure 20:
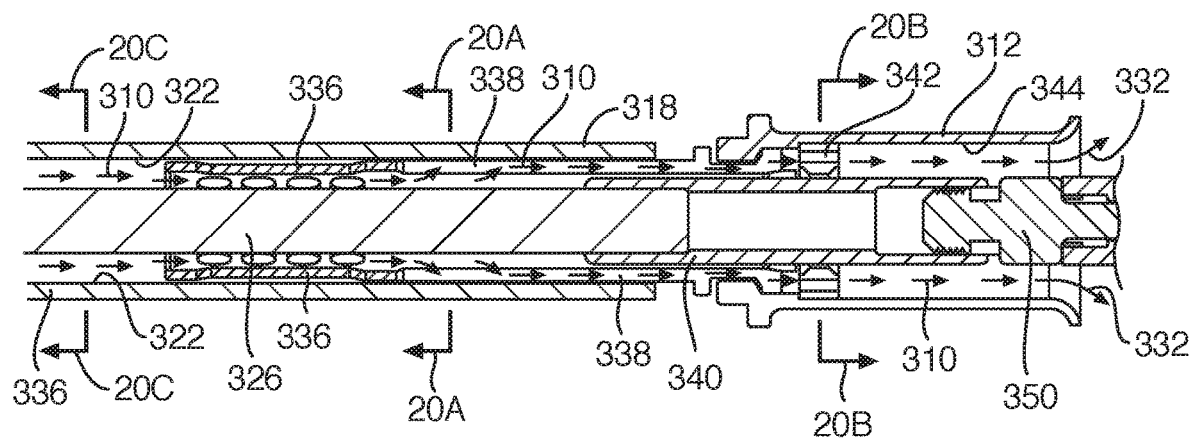
FIG. 20 is an enlarged cross-sectional view of the distal portion of the delivery system and the hub of the medical device (with the occluder portion removed for simplification purposes), depicting a flow path of the contrast fluid moving through the delivery system and hub of the medical device, according to another embodiment of the present invention.

Now with reference to FIGS. 18 through 20, another embodiment of a medical device 300 and a medical device delivery system 302 for modifying an LAA 5 of the heart that facilitates imaging of the LAA 5 with contrast fluid 304 and an imaging device (not shown) is provided. In this embodiment, the structural components and functionality of the medical device 300 and the medical device delivery system 302 may be substantially similar to any one of the embodiments previously described. For example, the medical device 300 may include an occluder portion 306 and an anchor portion 308, similar to that described above.

In this embodiment, upon the medical device 300 being positioned within the LAA 5 with the anchor portion 308 deployed and engaged with tissue of the LAA 5, the medical device delivery system 302 and the medical device 300 may include a common flow path 310 defined therethrough for injecting a contrast fluid 304 through a hub 312 of the medical device 300 and to a distal side of the medical device 300 and into the LAA 5. One important aspect of this embodiment may be that the occluder portion 306 of the medical device includes a substantially non-permeable material of, for example, a polymeric material, such as foam and/or ePTFE, described in earlier embodiments herein as the tissue growth member. In one embodiment, the ePTFE may be the material that is non-permeable. In this manner, a physician can determine whether the contrast fluid 304 is being substantially maintained within the LAA 5 on the distal side of the medical device 300 to assess whether the medical device 300 is properly positioned within the LAA 5. Also, the physician can determine whether there are gaps between an outer periphery 314 of the medical device 300 and the tissue of the LAA 5 by viewing the contrast fluid 304 dissipating from the distal side of the medical device 300, as discussed in further detail below.

In one embodiment, the occluder portion 306 of the medical device 300 may include a polymeric material, such as the before-described foam and/or ePTFE. In another embodiment, the polymeric material may include a bio-agent coated over or impregnated within the polymeric material. Such bio-agent may be configured to enhance tissue growth and endothelization over the proximal side of the occluder portion 306 of the medical device 300. In another embodiment, the polymeric material may include a coating thereon that may be an anti-thrombotic coating, such as Heprin. In still another embodiment, the occluder portion may include a biological tissue, in addition to or instead of the before-described polymeric material. Such biological tissue may be a biological sourced tissue, such as pericardial tissue and/or peritoneum tissue, or any suitable biological tissue that is biocompatible as known in the art. Further, the biological tissue may be non-permeable, strong, and thin so as to readily be moved with the occluder portion frame structure between collapsed and expanded configurations. Further, the non-permeable characteristics of the pericardial tissue may function to substantially maintain contrast fluid 304 in the LAA 5 upon the medical device being positioned in the LAA. In another embodiment, the biological tissue may be permeable or include portions with permeable characteristics and other portions with non-permeable characteristics.

With reference to FIGS. 18, 18A and 18B, the medical device delivery system 302 includes a sheath 316, a delivery catheter 318 coupled to a handle 320, and the medical device 300 coupled to a distal end of the delivery catheter 318, similar to that described and depicted relative to FIG. 4 herein (as well as other embodiments herein). The delivery catheter 318 extends between a proximal end and a distal end such that the proximal end is coupled to the handle 320 and the distal end of the delivery catheter 318 is coupled to the implantable medical device 300. Further, the delivery catheter 318 defines a lumen 322 extending along a longitudinal length of the delivery catheter 318. The handle 320 may include a fluid port 324 sized and configured to directly communicate with the lumen 322 of the delivery catheter 318. Also, the delivery catheter 318 may include an actuator shaft 326 (coupled to the handle 320 and actuatable by the actuator knob 321) extending therethrough for controlling actuation of the anchor portion 308 of the medical device 300. With this arrangement, fluid, such as contrast fluid 304, may be injected through the fluid port 324 of the handle 320 and directly through the lumen 322 of the delivery catheter 318 such that the contrast fluid 304 may advance toward the medical device 300. The contrast fluid 304 may be a radio opaque fluid or dye (or any other suitable contrast fluid) that is viewable through imaging techniques, such as fluoroscopy or any other suitable imaging technique, as known to one of ordinary skill in the art.

As in previous embodiments, the delivery catheter 318 and the medical device 300 coupled at the distal end thereof may be sized and configured to be pushed through a sheath lumen 317 defined along a length of the sheath 316. The sheath 316 may also include a sheath fluid port 328 sized and configured to inject fluid, such as contrast fluid 304, through the sheath lumen 317 and to exit from the distal end of the sheath 316. Such injection of contrast fluid 304 through the sheath lumen 317 via the sheath fluid port 328 may provide additional information to the physician relative to imaging a proximal side of the medical device 300 upon being positioned in the LAA, discussed further herein.

The fluid, such as contrast fluid 304, may be injected through the fluid port 324 of the handle 320, as well as the sheath fluid port 328 of the sheath 316, with an injection device 330. In one embodiment, the injection device 330 may be a syringe for manual injection through the fluid port 324 of the handle 320 or through the sheath fluid port 328 of the sheath 316. In another embodiment, the injection device 330 may include an injection machine that controls the pressure, amount, and/or flow rate of fluid being injected through the fluid port 324 of the handle 320 (or through the sheath fluid port 328 of the sheath 316), as known to one of ordinary skill in the art.

Now with reference to FIGS. 19 and 20, fluid, such as contrast fluid 304, may flow through the lumen 322 of the delivery catheter 318, as discussed above, and through the hub 312 (and components associated therewith) of the medical device 300, the medial device 300 being positioned in the LAA 5. As the contrast fluid 304 exits the hub 312 of the medical device 300, as depicted by arrows 332 in FIG. 19, the contrast fluid 304 mixes with the blood in the LAA 5 and is viewable via real-time imaging techniques, such as with a fluoroscopy or the like. Due to the occluder portion 306 having the substantially non-permeable material associated therewith, if the medical device 300 is properly positioned in the LAA 5, the contrast fluid 304 may be substantially maintained within the LAA 5, but for general seeping around the outer periphery 314 of the medical device 300 without an identifiable source or gap. In this manner, the physician can readily identify if the medical device is properly positioned within the LAA by viewing the contrast fluid 304 substantially maintained on a distal side of the medical device. The meaning of substantially maintaining contrast fluid 304 in the LAA means substantially containing, sustaining and/or retaining the contrast fluid in the LAA, except for general seeping along the outer periphery 314.

If there is a gap between the outer periphery 314 of the medical device 300 and the tissue of the LAA 5, the physician will readily ascertain and identify such gap due to the contrast fluid 304 moving through a localized portion from the LAA 5 such that contrast fluid is viewable in a concentrated flow or jet escaping the LAA 5 and moving proximally past the outer periphery 314 of the medical device 300. If the physician determines there is a gap, the physician can readily retract the anchor portion 308 and re-position the medical device 300 in the LAA 5 and then deploy the anchor portion 308 to engage the tissue in the LAA 5, as discussed in detail herein. The physician may then inject additional contrast fluid 304 through the hub 312 of the medical device 300 to determine if the medical device 300 is properly positioned. In addition, the physician may also inject contrast fluid 304 through the sheath 316 via the sheath fluid port 328, as previously discussed, to view a proximal side of the medical device 300 in the LAA 5, thereby, obtaining additional information relative to the position of the medical device 300 in the LAA 5. Once the physician is satisfied with the position of the medical device 300, the delivery catheter 318 may be de-coupled or detached from the medical device 300, as previously set forth herein.

Figure 20A:
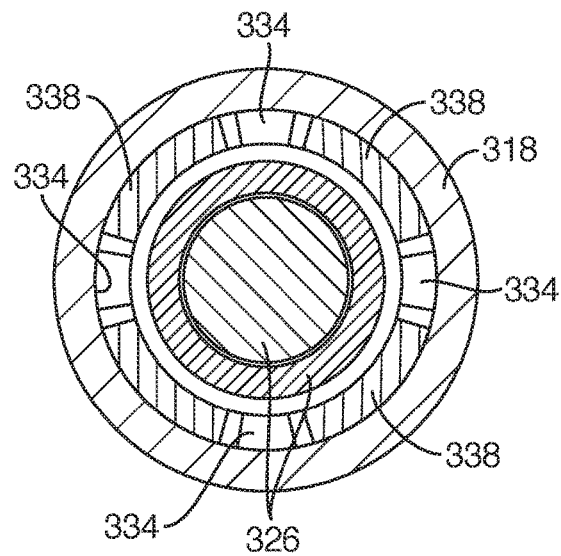
FIG. 20A is an enlarged cross-sectional view taken from region 20A of FIG. 20, depicting the flow path for the contrast fluid at a distal portion of the delivery system, according to another embodiment of the present invention.
Figure 20B:
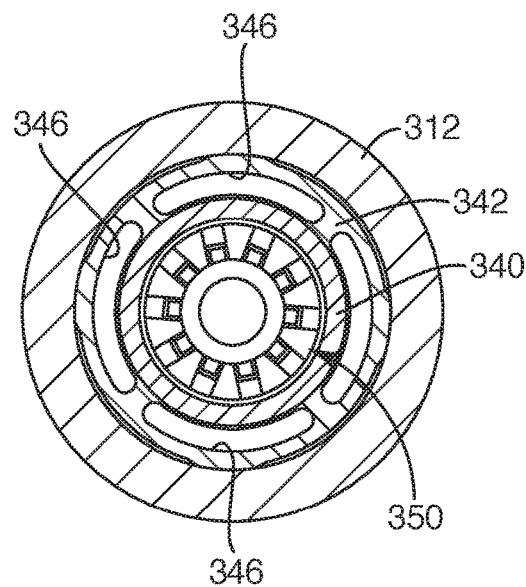
FIG. 20B is an enlarged cross-sectional view taken from region 20B of FIG. 20, depicting the flow path for the contrast fluid at the hub of the medical device, according to another embodiment of the present invention.

With respect to FIGS. 20, 20A, and 20B, the flow path (depicted by arrows 310 in FIG. 20) of the contrast fluid 304 flowing from the delivery catheter 318 and through the hub 312 will now be described. The flow path 310 extends through the lumen 322 of the delivery catheter 318 and surrounds and moves along a length of the actuator shaft 326 and the delivery catheter 318. Section 20C identified in FIG. 20 may be substantially similar to that described and depicted in FIG. 18A, depicting the delivery catheter 318 defining the lumen 322 with the actuator shaft 326 positioned therethrough. The flow path 310 continues to advance along the collet 336 and then outward into a space 334 or channel defined between the collet fingers 338 (see FIGS. 20 and 20A). The flow path 310 continues advancing between an inner distal connector 340 and the delivery catheter 318 and then between the inner distal connector 340 and the medical device 300 (only the hub 312 is shown), as depicted in FIGS. 20 and 20A. The hub 312 includes a guide ring 342 that may be embedded within the inner diameter or bore 344 defined in the hub 312 itself. Such guide ring 342 includes apertures 346 (see FIG. 20B) defined therein through which the flow path 310 extends. Such apertures 346 may include an annular space or partial annular configuration or space. In another embodiment, the inner diameter or bore may include an annular protrusion, instead of the guide ring 342, such that the bore 344 between the annular protrusion and the inner distal connector 340 may define an annular space through which the flow path 310 extends (instead of the apertures 346). Once the flow path 310 continues through the apertures 346 or annular space and past the guide ring 342 or annular protrusion in the bore 344, the flow path 310 continues advancing through the bore 344 of the hub 312 and distally over the inner distal connector 340. The inner distal connector 340 may include threads along an inner diameter thereof to couple to threads on a proximal end of the anchor hub 350. The flow path 310 continues advancing through the hub 312 until exiting the hub 312, as depicted with arrows 332, so that contrast fluid 304 can enter the LAA 5 on the distal side of the medical device 300, as shown in FIG. 19. With this arrangement, each of the handle 320, delivery catheter 318 and hub 312 of the medical device 300 includes a common, shared, or corresponding flow path 310 that facilitates contrast fluid 304 to exit a distal side of the medical device 300. As such, a physician may view the medical device 300 positioned in the LAA 5 to determine if the contrast fluid 304 is being substantially maintained within the LAA (since the occluder portion includes a non-permeable material), but for minor general seeping along the outer periphery 314 of the medical device 300 contacting the LAA 5. In this manner, the physician can obtain additional imaging information to ascertain whether the medical device 300 is properly positioned in the LAA 5.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes all modifications, equivalents, and alternatives falling within the spirit and scope of the invention as defined by the following appended claims.

What is claimed is:

1. A method for modifying a left atrial appendage ("LAA") of a heart, the method comprising:
   anchoring a medical device in the LAA with a delivery catheter directly coupled to a hub of the medical device such that the medical device includes an occluder material extending over a proximal side of medical device with occluder material flaps adjacent the hub in an open first position, the medical device having a spring element positioned over the hub and enveloped at least partially by the occluder material flaps; and
   detaching the catheter from the hub of the medical device such that the occluder material flaps adjacent the hub automatically move to a closed second position to close-off the hub of the medical device.

2. The method according to claim 1, wherein the anchoring comprises anchoring the medical device with the occluder material being a polymeric material.

3. The method according to claim 1, wherein the detaching comprises unthreading the catheter from the medical device.

4. The method according to claim 1, wherein the detaching comprises detaching the catheter having threads from a threaded portion of the medical device.

5. The method according to claim 1, wherein the detaching comprises closing a bore of the hub with the occluder material flaps being biased to the closed position such that the occluder material flaps substantially eliminate exposure of metallic material on the proximal side of the medical device at the hub of the medical device.

6. A method for modifying a left atrial appendage ("LAA") of a heart, the method comprising:
   anchoring a medical device in the LAA with a delivery catheter coupled to a hub of the medical device such that the medical device includes a moveable portion positioned adjacent the hub and moveable between an open first position and a closed second position, the moveable portion in the open first position with the delivery catheter coupled to the medical device, the moveable portion having a spring element adjacent the hub and biased toward a flat configuration; and
   detaching the delivery catheter from the hub of the medical device such that the moveable portion adjacent the hub automatically moves to the closed second position to close-off the hub of the medical device.

7. The method according to claim 6, wherein the anchoring comprises anchoring the medical device including the moveable portion having the spring element, the spring element biased upon being in the open first position and the spring element relaxed upon being in the closed second position.

8. The method according to claim 6, wherein the anchoring comprises anchoring the medical device with a polymeric material positioned at least partially over a proximal side of the medical device.

9. The method according to claim 6, wherein the detaching comprises unthreading the delivery catheter from the medical device.

10. The method according to claim 6, wherein the detaching comprises detaching the delivery catheter having threads from a threaded portion of the medical device.

11. The method according to claim 6, wherein the detaching comprises closing a bore of the hub with the moveable portion being biased to the closed position such that the moveable portion substantially eliminates exposure of metallic material on the proximal side of the medical device at the hub of the medical device.

12. The method according to claim 6, wherein the anchoring comprises anchoring the medical device with the moveable portion defining material flaps sized to at least partially envelope the spring element.

13. A method for closing-off an opening, the method comprising:

anchoring a medical device in the opening with a delivery catheter coupled to a hub of the medical device such that the medical device includes a moveable portion positioned adjacent the hub, the moveable portion being moveable between an open first position and a closed second position, the moveable portion being in the open first position with the delivery catheter coupled to the medical device, the moveable portion having a spring element positioned adjacent the hub and biased toward the closed position; and detaching the delivery catheter from the hub of the medical device such that the spring element adjacent the hub automatically moves the moveable portion to the closed second position to cover a proximal side of the hub of the medical device.

14. The method according to claim 13, wherein the anchoring comprises anchoring the medical device with the moveable portion defining material flaps sized to at least partially envelope the spring element.

15. The method according to claim 14, wherein the anchoring comprises anchoring the medical device such that the material flaps are spaced apart in the open first position and, upon detaching the delivery catheter from the hub, the material flaps move to an overlapping configuration in the closed second position.

16. The method according to claim 13, wherein the anchoring comprises anchoring the medical device with the moveable portion including a polymeric material.

17. The method according to claim 13, wherein the anchoring comprises anchoring the medical device with the moveable portion defining material flaps sized to at least partially envelope the spring element.

18. The method according to claim 13, wherein the detaching comprises unthreading the delivery catheter from the medical device.

19. The method according to claim 13, wherein the detaching comprises detaching the delivery catheter having threads from a threaded portion of the medical device.

20. The method according to claim 13, wherein the detaching comprises closing a bore of the hub with the moveable portion being biased to the closed position such that the moveable portion defines flaps that cover metallic material on the proximal side of the medical device at the hub of the medical device.

* * * * *